(12) United States Patent
Sohn et al.

(10) Patent No.: US 8,902,412 B2
(45) Date of Patent: Dec. 2, 2014

(54) DEFECT INSPECTION APPARATUS AND DEFECT INSPECTION METHOD USING THE SAME

(75) Inventors: Young-Hoon Sohn, Seongnam-si (KR); Yu-Sin Yang, Seoul (KR); Sang-Kil Lee, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 284 days.

(21) Appl. No.: 13/472,145

(22) Filed: May 15, 2012

(65) Prior Publication Data
US 2012/0314205 A1 Dec. 13, 2012

(30) Foreign Application Priority Data

Jun. 8, 2011 (KR) .......................... 10-2011-0055210

(51) Int. Cl.
*G01N 21/00* (2006.01)
*G01N 21/55* (2014.01)
*G01N 21/95* (2006.01)

(52) U.S. Cl.
CPC ............ *G01N 21/55* (2013.01); *G01N 21/9501* (2013.01)

USPC ........................................................... 356/72

(58) Field of Classification Search
USPC ....................................................... 356/72–73
See application file for complete search history.

(56) References Cited

U.S. PATENT DOCUMENTS 6,317,514 B1 * 11/2001 Reinhorn et al. ............. 382/147

FOREIGN PATENT DOCUMENTS

| JP | 2000-31228 A | 1/2000 |
| JP | 2002-296314 A | 10/2002 |
| JP | 2005-32760 A | 2/2005 |

* cited by examiner

*Primary Examiner* — Abdullahi Nur
(74) *Attorney, Agent, or Firm* — Sughrue Mion, PLLC

(57) ABSTRACT

A defect inspection apparatus comprises a table on which a substrate is placed, a first detection unit which is disposed above the table to detect an optical signal from the substrate, a second detection unit which is disposed above the table to detect an electrical signal from the substrate, and a signal processing unit which is connected to the first detection unit and the second detection unit to detect a chemical defect using the optical signal and the electrical signal.

19 Claims, 22 Drawing Sheets

$E_F$ : FERMI ENERGY OF ELECTRON
$\Phi$ : WORK FUNCTION $R_E > R_0$ $R_E \doteq R_O$

|     | OPTICAL SIGNAL | ELECTRICAL SIGNAL | CHEMICAL DEFECT |
|-----|----------------|-------------------|-----------------|
| (a) | X              | X                 | X               |
| (b) | O              | O                 | X               |
| (c) | X              | O                 | O               |
| (d) | O              | X                 | X               |

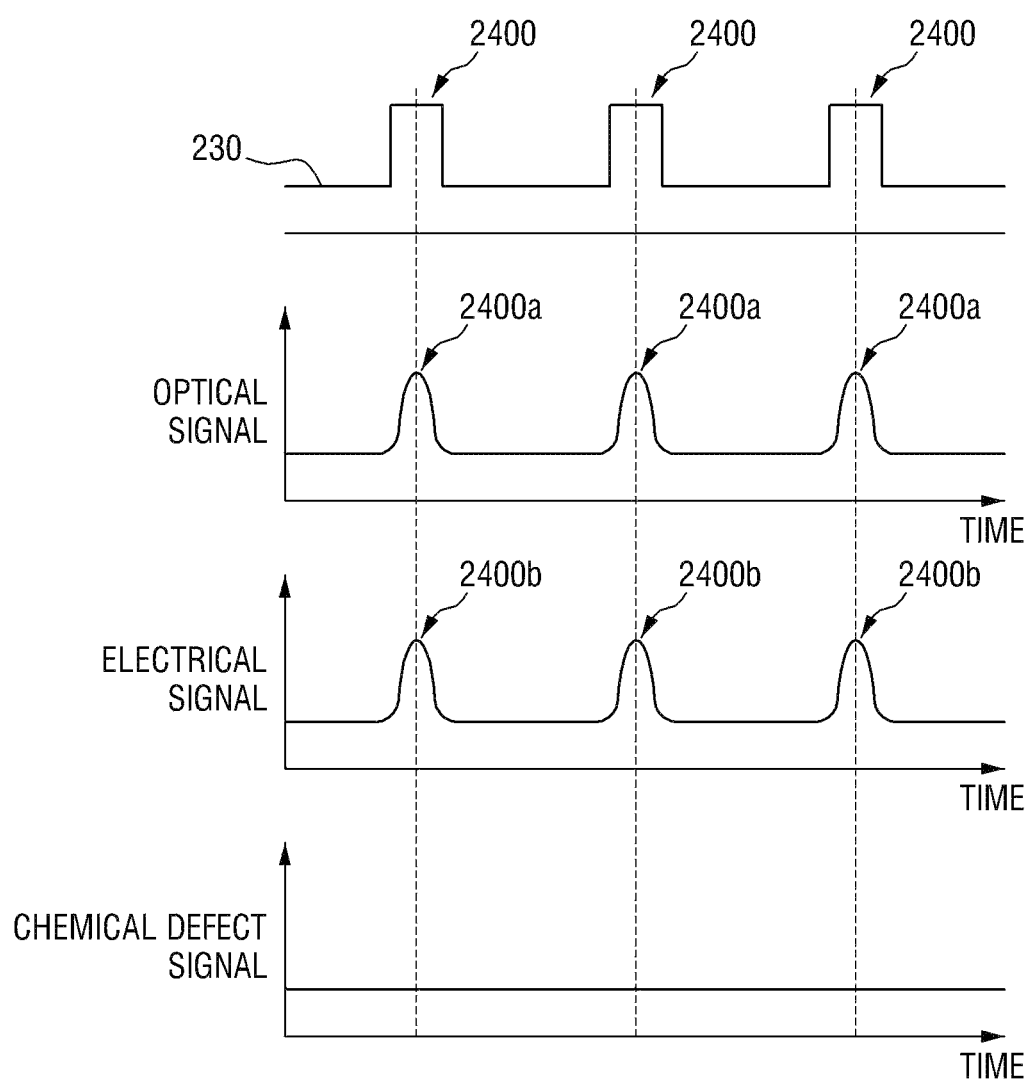

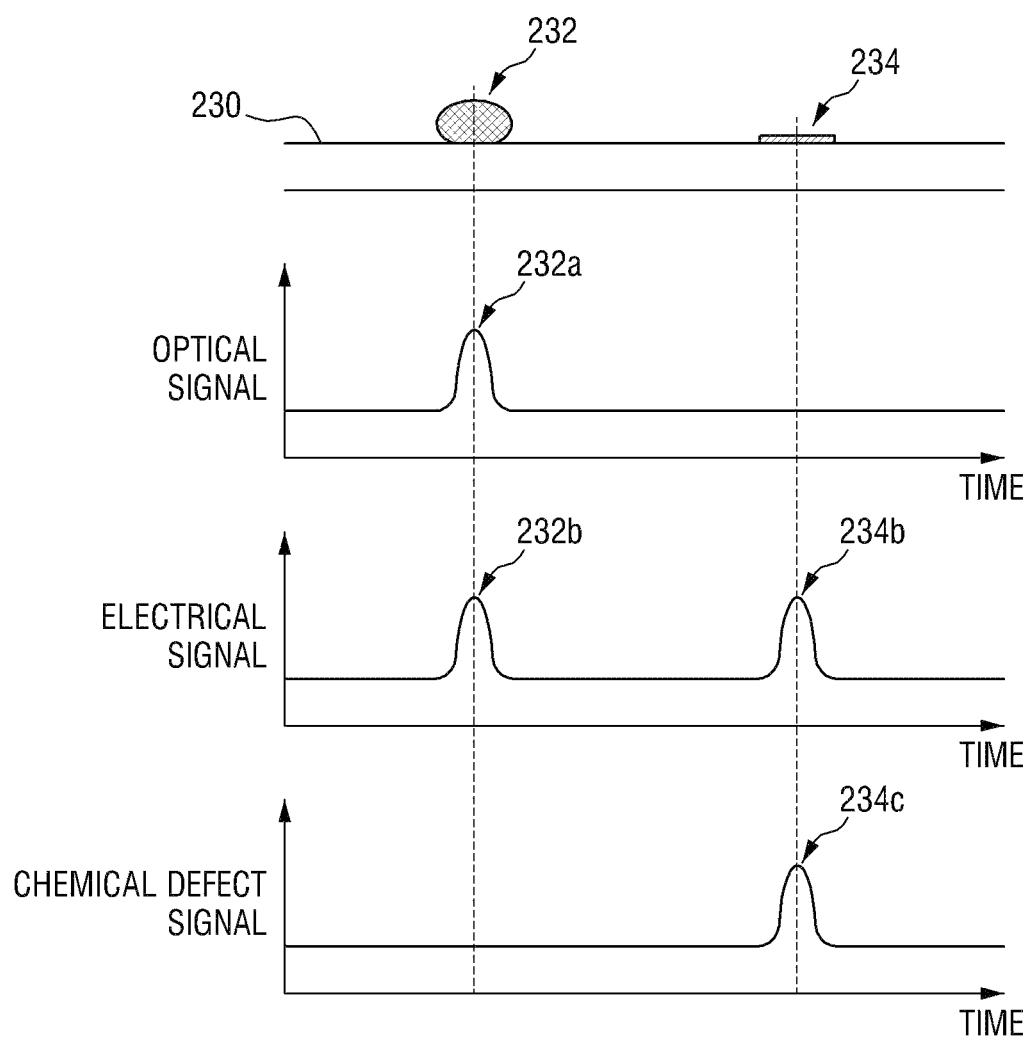

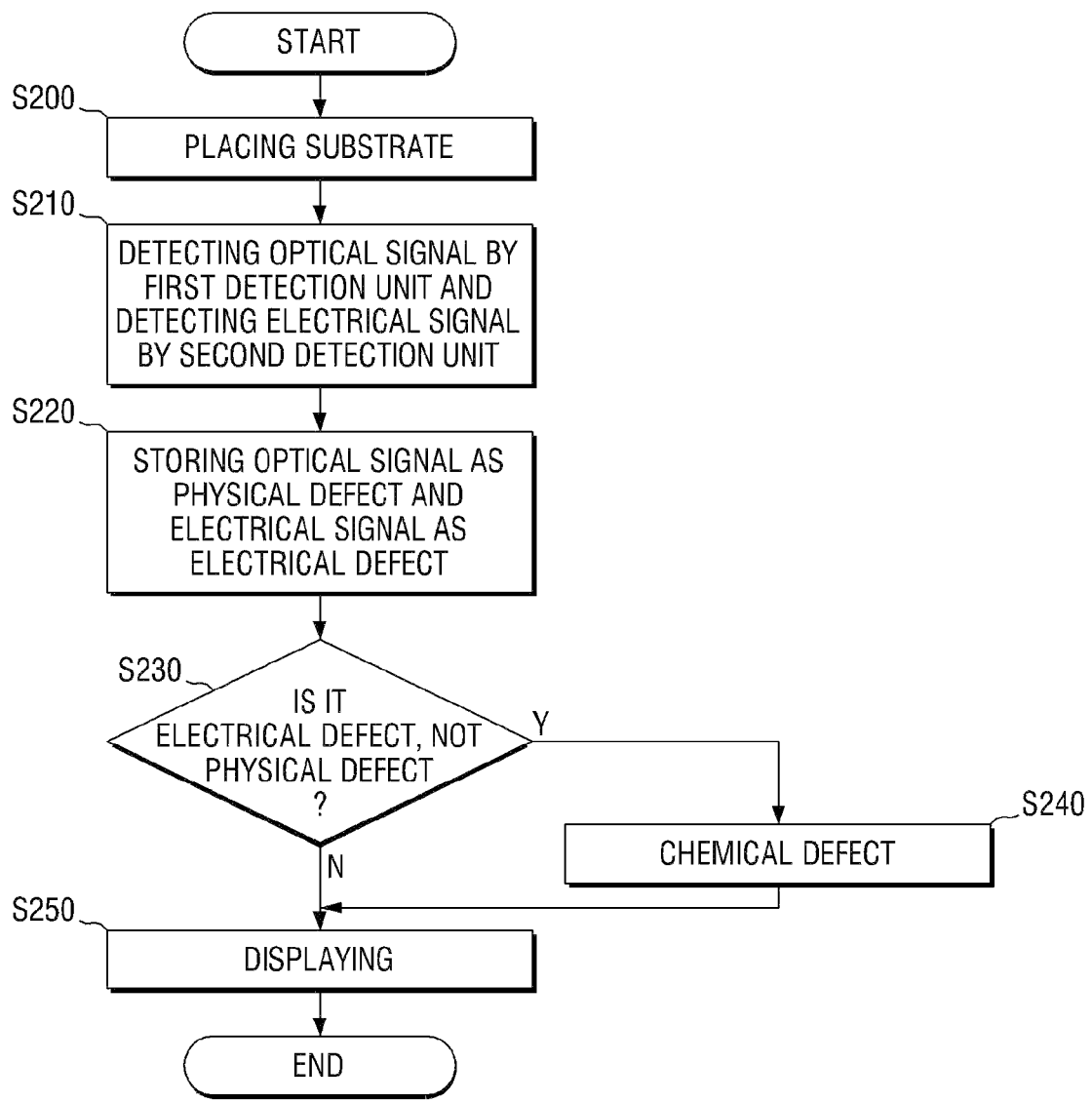

US 8,902,412 B2

DEFECT INSPECTION APPARATUS AND DEFECT INSPECTION METHOD USING THE SAME

CROSS-REFERENCE TO RELATED APPLICATION

This application claims priority from Korean Patent Application No. 10-2011-0055210 filed on Jun. 8, 2011 in the Korean Intellectual Property Office, and all the benefits accruing therefrom under 35 U.S.C. 119, the contents of which in its entirety are herein incorporated by reference.

BACKGROUND

1. Field of Endeavor

The present application relates to a defect inspection apparatus and a defect inspection method using the same.

2. Description of the Related Art

Recently, as a semiconductor process becomes finer and more delicate, yield and reliability of a product are increasingly being affected by a defect generated in the process. Accordingly, a precision is required for a process of detecting a defect generated in a semiconductor manufacturing process.

In a method for optically inspecting the surface of a substrate, a defect having a physical shape (hereinafter, a physical defect) can be detected, but a defect having no shape (hereinafter, a chemical defect) such as organic or inorganic contamination and residues cannot be detected. Such chemical defect can be detected by measuring abnormality of an electrical signal of the surface of the substrate. However, the abnormality of the electrical signal may be measured for not only a chemical defect but also a physical defect. Accordingly, in case of determining a chemical defect using an electrical signal, it inevitably requires a checking operation such as additional optical inspection or chemical component analysis, e.g., total reflection X-ray fluorescence (TXRF), secondary ion mass spectroscopy (SIMS) or energy dispersive spectroscopy (EDS).

SUMMARY

The present invention provides a defect inspection apparatus capable of detecting a chemical defect using an optical signal and an electrical signal of a substrate.

The present invention also provides a defect inspection method capable of detecting a chemical defect using an optical signal and an electrical signal of a substrate.

The objects of the present invention are not limited thereto, and the other objects of the present invention will be described in or be apparent from the following description of the embodiments.

According to an aspect of the present invention, there is provided a defect inspection apparatus, comprising a table on which a substrate is placed, a first detection unit disposed above the table which detects an optical signal from the substrate, a second detection unit disposed above the table which detects an electrical signal from the substrate, and a signal processing unit connected to the first detection unit and the second detection unit which detects a chemical defect using the optical signal and the electrical signal.

According to another aspect of the present invention, there is provided a defect inspection apparatus, comprising a table on which a substrate is placed, a first detection unit and a second detection unit which are disposed above the table to detect an optical signal from an inspection region of the substrate and an electrical signal from the inspection region of the substrate, respectively, and a signal processing unit connected to the first detection unit and the second detection unit to process the optical signal and the electrical signal.

According to another aspect of the present invention, there is provided a method of detecting a chemical defect in a substrate, comprising a substrate, an optical sensor which generates an optical signal based on light reflected from a region of the substrate, an electrical sensor which generates an electrical signal by measuring the voltage difference between the region of the substrate and a fixed voltage, and a signal processor which detects a chemical defect based on a comparison of the optical signal and the electrical signal.

BRIEF DESCRIPTION OF THE DRAWINGS

The above and other aspects and features of the present invention will become more apparent by describing in detail exemplary embodiments thereof with reference to the attached drawings, in which:

FIGS. 14 to 16 are diagrams for explaining a defect inspection method in accordance with the embodiment of the present invention.

DETAILED DESCRIPTION OF THE EMBODIMENTS

Figure 1:
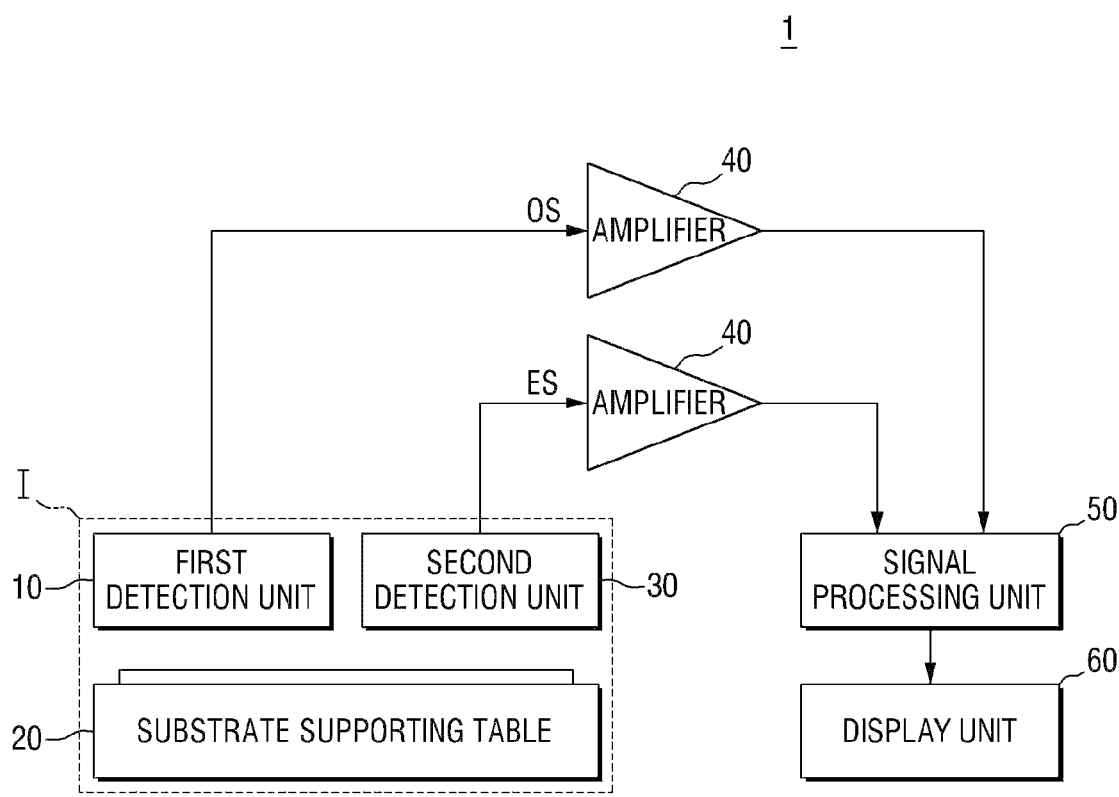
FIG. 1 illustrates a block diagram of a defect inspection apparatus in accordance with an embodiment of the present invention.

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will filly convey the scope of the invention to those skilled in the art. The same reference numbers indicate the same components throughout the specification. In the attached figures, the thickness of layers and regions is exaggerated for clarity.

It will be understood that when an element or layer is referred to as being "connected to," or "coupled to" another element or layer, it can be directly connected to or coupled to another element or layer or intervening elements or layers may be present. In contrast, when an element is referred to as being "directly connected to" or "directly coupled to" another element or layer, there are no intervening elements or layers present. Like numbers refer to like elements throughout. As used herein, the term "and/or" includes any and all combinations of one or more of the associated listed items.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

It will be understood that, although the terms first, second, etc. may be used herein to describe various elements, these elements should not be limited by these terms. These terms are only used to distinguish one element from another element. Thus, for example, a first element, a first component or a first section discussed below could be termed a second element, a second component or a second section without departing from the teachings of the present invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Unless defined otherwise, all technical and scientific terms used herein have the same meaning as commonly understood by one of ordinary skill in the art to which this invention belongs. It is noted that the use of any and all examples, or exemplary terms provided herein is intended merely to better illuminate the invention and is not a limitation on the scope of the invention unless otherwise specified. Further, unless defined otherwise, all terms defined in generally used dictionaries may not be overly interpreted.

Hereinafter, a defect inspection apparatus in accordance with an embodiment of the present invention will be described with reference to FIGS. 1 to 8C.

Figure 2:
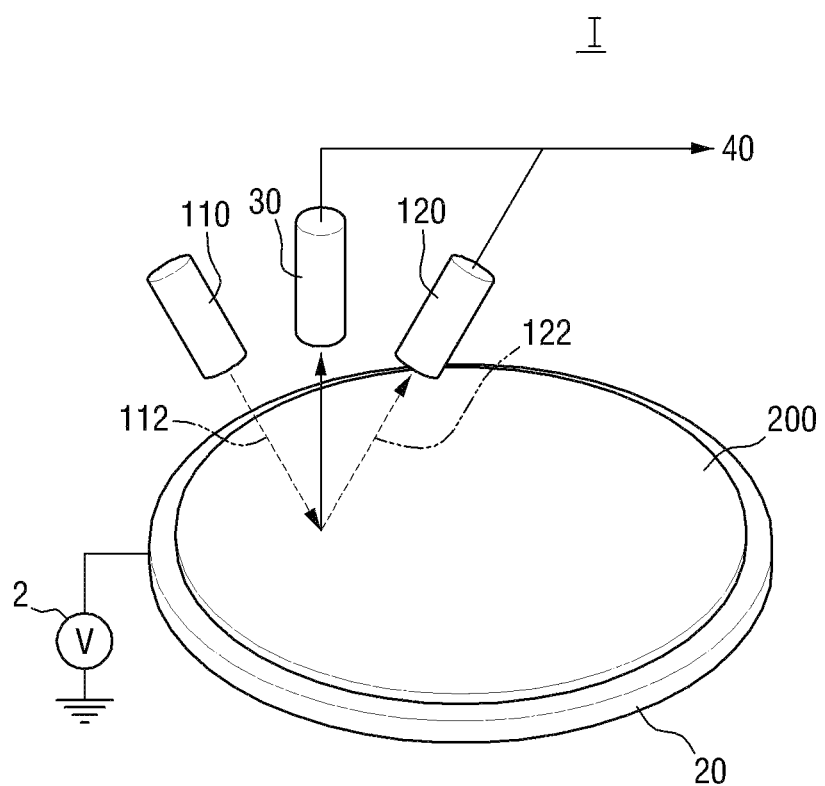
FIG. 2 illustrates a detailed configuration of portion I of FIG. 1.
Figure 3:
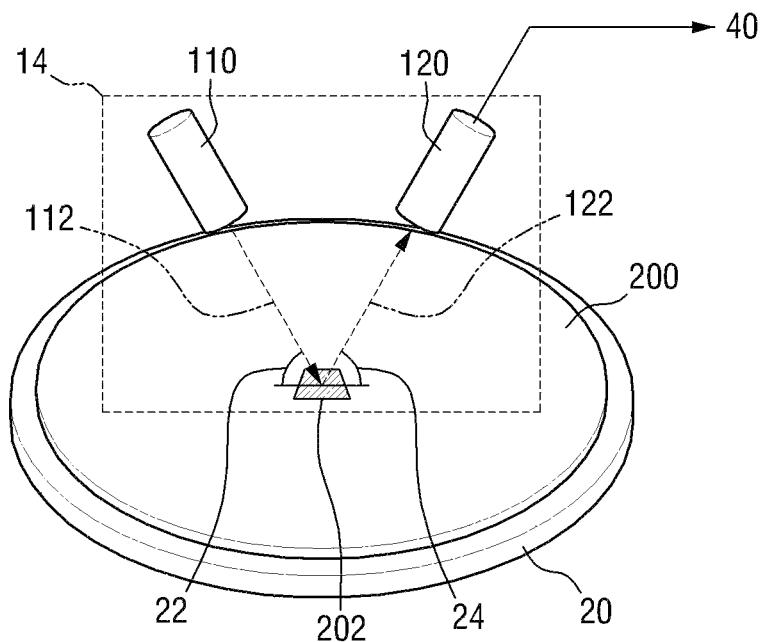
FIG. 3 is a diagram for explaining an operation of a first detection unit of FIG. 1.
Figure 4A:
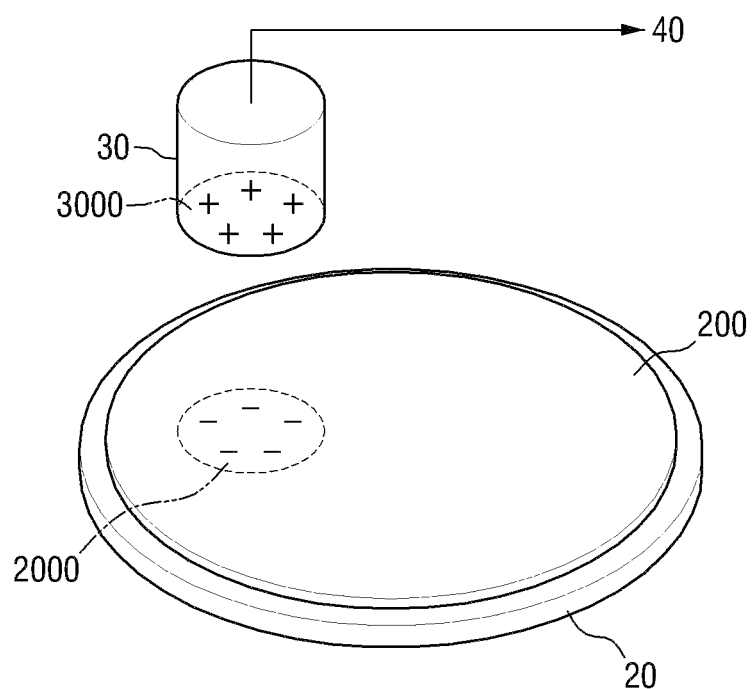
FIGS. 4A and 4B are diagrams for explaining an operation of a second detection unit of FIG. 1.
Figure 4B:
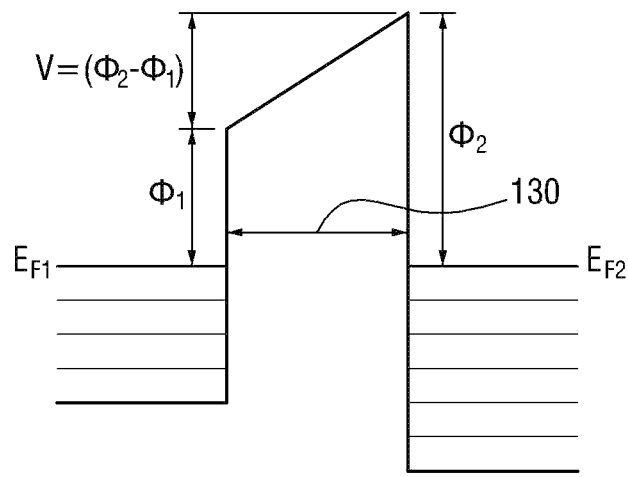
Figure 5A:
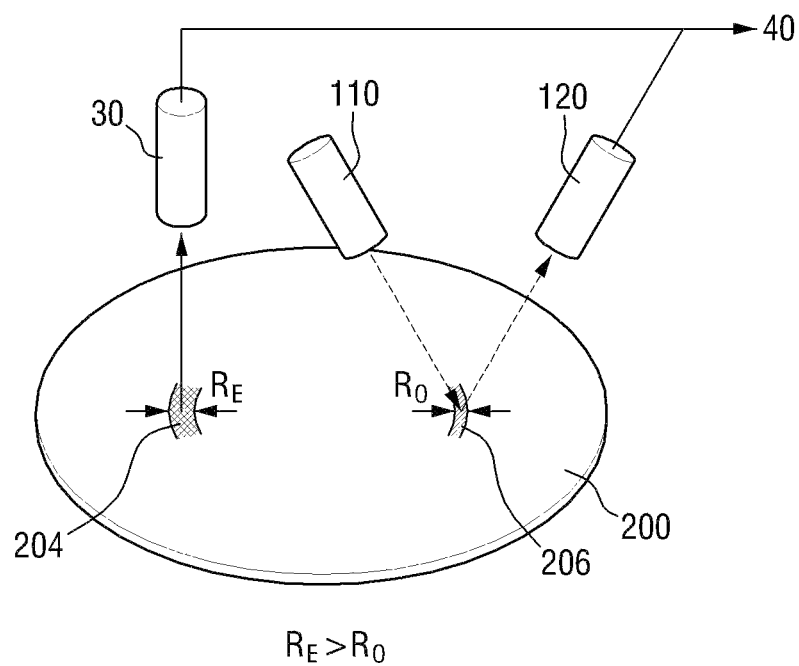
FIGS. 5A and 5B are diagrams for explaining detection regions of the first detection unit and the second detection of FIG. 1.
Figure 5B:
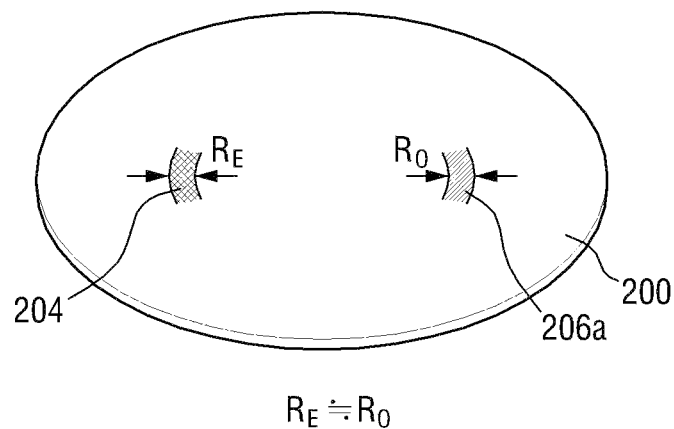
Figure 6A:
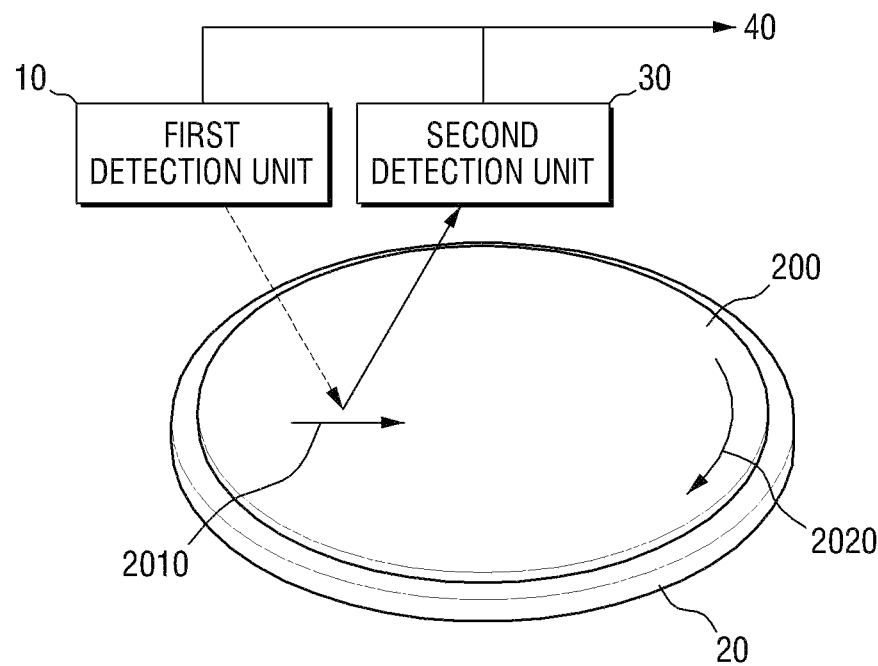
FIGS. 6A and 6B are diagrams for explaining a relationship among the first detection unit, the second detection unit and a substrate supporting table of FIG. 1.
Figure 6B:
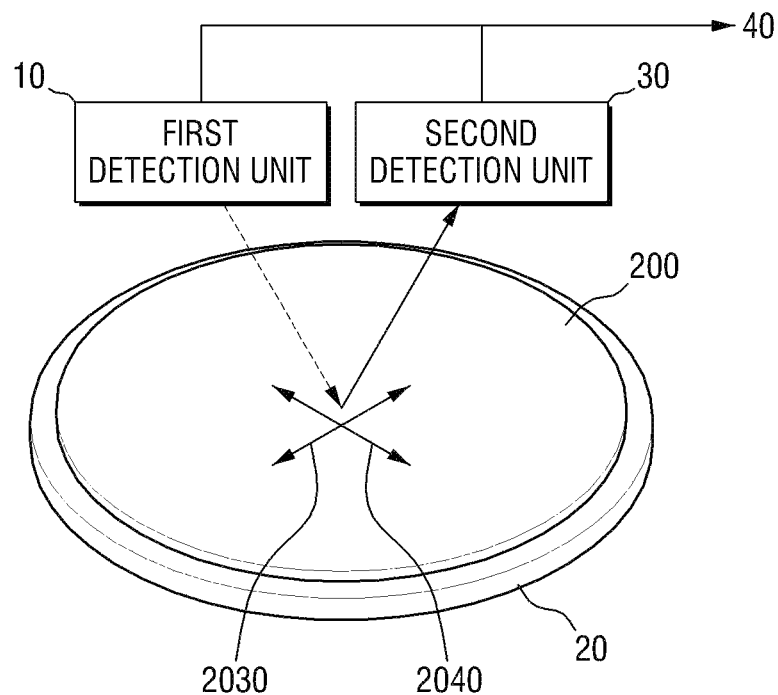
Figure 7:
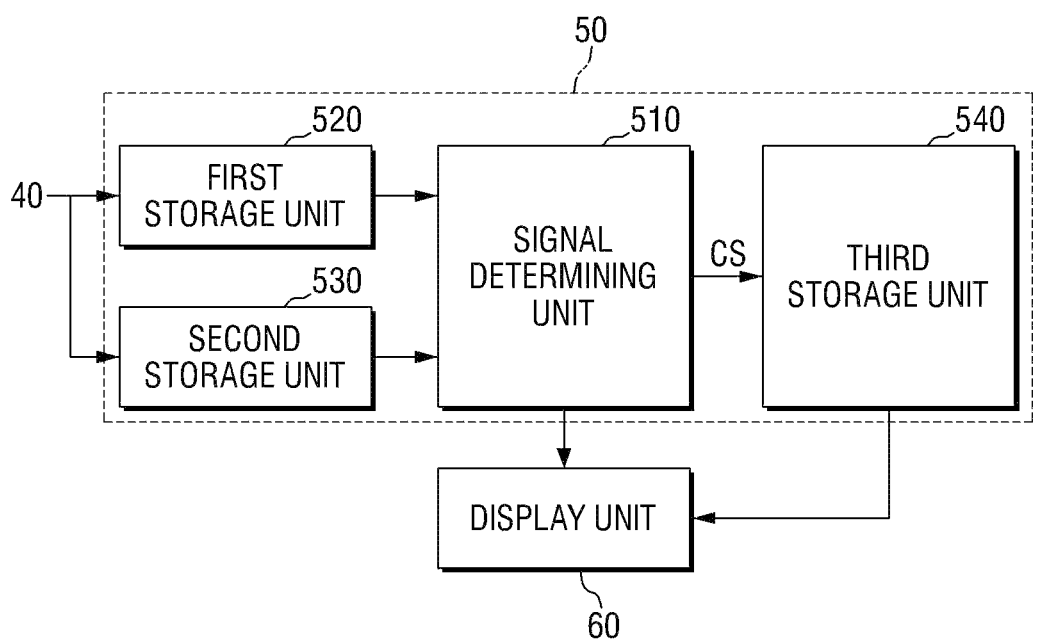
FIG. 7 is a block diagram showing a configuration of a signal processing unit of FIG. 1.
Figure 8A:
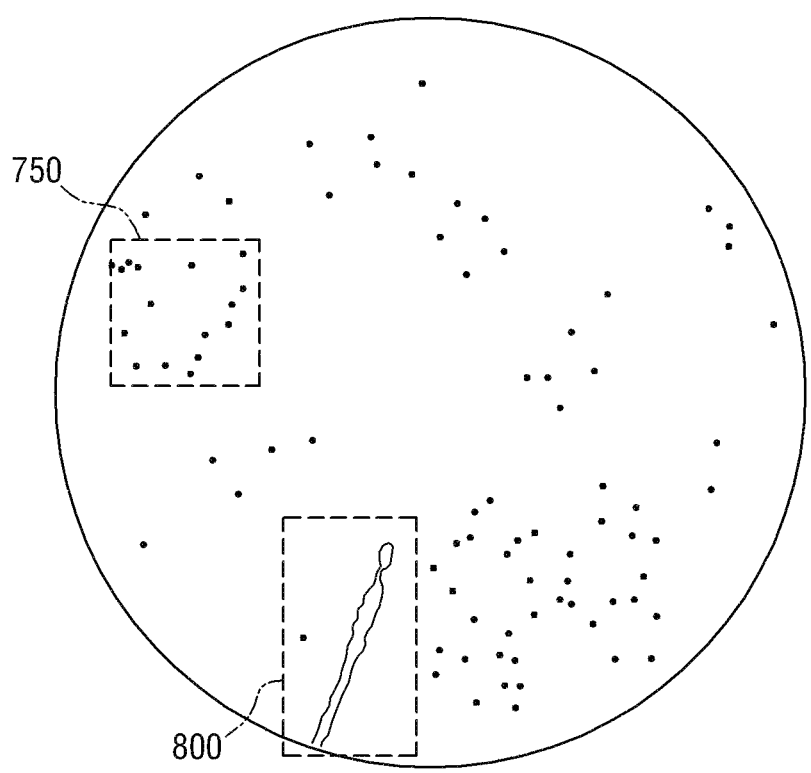
FIGS. 8A to 8C illustratively show a defect detected in a display unit of FIG. 1.
Figure 8B:
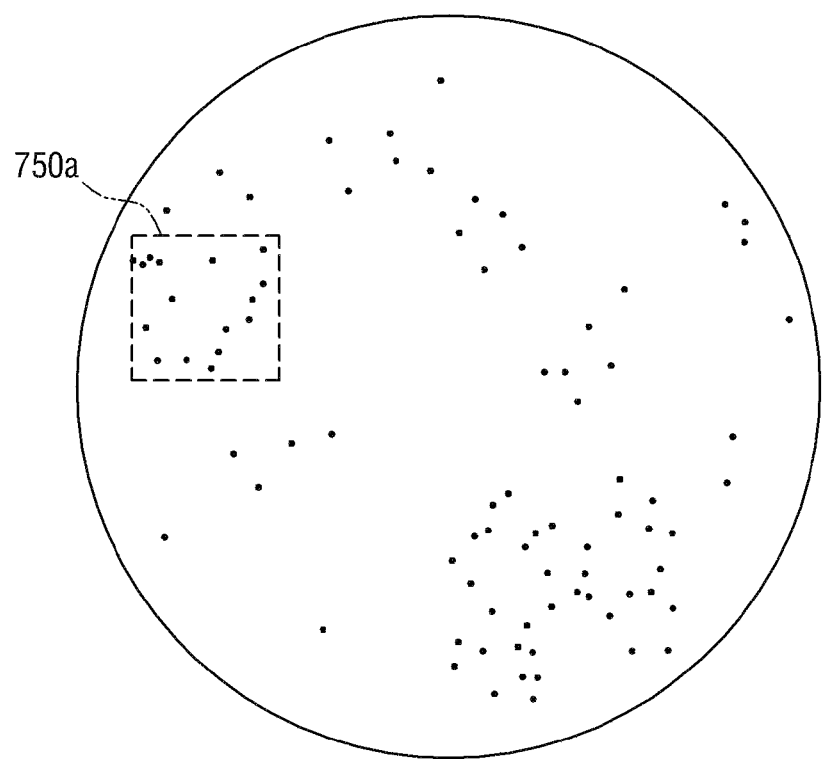
Figure 8C:
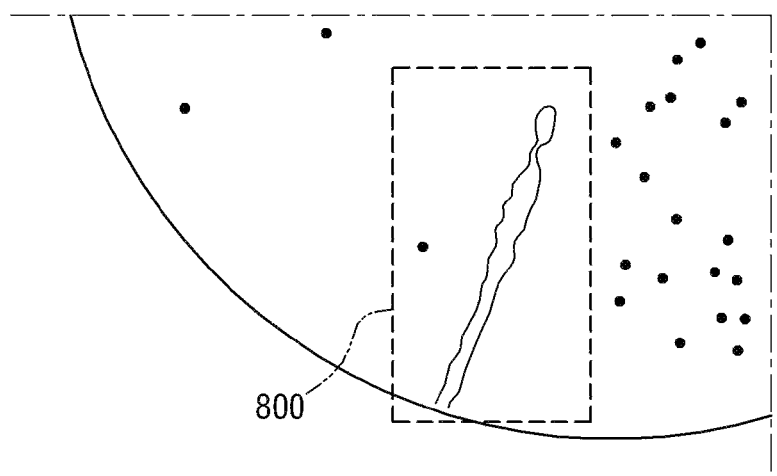

FIG. 1 illustrates a block diagram of the defect inspection apparatus in accordance with the embodiment of the present invention. FIG. 2 illustrates a detailed configuration of portion I of FIG. 1. FIG. 3 is a diagram for explaining an operation of a first detection unit of FIG. 1. FIGS. 4A and 4B are diagrams for explaining an operation of a second detection unit of FIG. 1. FIGS. 5A and 5B are diagrams for explaining detection regions of the first detection unit and the second detection of FIG. 1. FIGS. 6A and 6B are diagrams for explaining a relationship among the first detection unit, the second detection unit and a substrate supporting table of FIG. 1. FIG. 7 is a block diagram showing a configuration of a signal processing unit of FIG. 1. FIGS. 8A to 8C illustratively show a defect detected in a display unit of FIG. 1.

First, referring to FIGS. 1 and 2, a defect inspection apparatus 1 in accordance with the embodiment of the present invention includes a substrate supporting table 20, a first detection unit 10, a second detection unit 30, amplifiers 40, a signal processing unit 50, and a display unit 60. The amplifiers 40 may be provided as separate components, or may be included in the signal processing unit 50.

The substrate supporting table 20 is a place on which a substrate to be inspected is disposed. The first detection unit 10 is disposed above the substrate supporting table 20 to detect an optical signal from the substrate. The second detection unit 30 is disposed above the substrate supporting table 20 to detect an electrical signal from the substrate. Further, the signal processing unit 50 is connected to the first detection unit 10 and the second detection unit 30 to detect a chemical defect using the optical signal and the electrical signal.

A substrate 200 to be inspected is placed on the substrate supporting table 20. Specifically, the substrate 200 may include a pattern or may have a substantially flat surface without a pattern. The substrate 200 may be a silicon substrate, a silicon germanium substrate, a silicon on insulator (SOI) substrate, a gallium arsenic substrate, a rigid substrate such as a glass substrate for display, a flexible substrate or the like, but it is not limited thereto.

The substrate supporting table 20 may be moved by a moving member (not shown). That is, it is possible to adjust a relative position between the substrate 200 and the first detection unit 10 and between the substrate 200 and the second detection unit 30 by moving the substrate supporting table 20. The moving member (not shown) may be located below the substrate supporting table, but it is not limited thereto.

Further, the substrate supporting table 20 may fix the substrate 200, e.g., in a vacuum manner. That is, the substrate supporting table 20 is connected to a vacuumizer (not shown), and the substrate 200 may be fixed by sucking air using the vacuumizer (not shown).

Meanwhile, the substrate supporting table 20 may be electrically connected to a first voltage 2. For example, the first voltage 2 may be a ground voltage, but it is not limited thereto.

The first detection unit 10 includes a light source 110 and a sensing unit 120 to detect an optical signal.

Specifically, the light source 110 is disposed above the substrate supporting table 20, and irradiates first light 112 onto the substrate 200. The first light 112 is reflected from the substrate 200 to generate second light 122. The sensing unit 120 is disposed above the substrate supporting table 20 to detect the second light 122. The sensing unit 120 may be connected to the amplifier 40, and the amplifier 40 amplifies the detected second light 122.

The light source 110 may be various types of light sources, e.g., a lamp and a laser generating light. Specifically, the lamp may be a light emitting diode (LED) lamp, a tungsten halogen lamp, a xenon lamp or the like, and the laser may be a helium-neon (HeNe) laser, an argon (Ar) laser, a laser diode (LD) having various wavelengths or the like, but it is not limited thereto.

Further, the light source 110 may be disposed above the substrate supporting table 20 while being fixed to or separated from a wall surface (not shown) of the defect inspection apparatus 1.

The sensing unit 120 senses light to generate an electrical signal. That is, the sensing unit 120 senses an optical signal to generate an electrical signal. Specifically, the sensing unit 120 may be formed of a photo transistor, or a photo diode such as a PIN diode and an APD diode, but it is not limited thereto.

Further, the sensing unit 120 for detecting an optical signal senses a variation in intensity of the second light 122 generated after the first light 112 is reflected. When the first light 112 is scattered by a physical defect and/or a pattern formed on the substrate 200, the intensity of the second light 122 may be changed. When only a part of the first light 112 is reflected by polarization of the substrate 200, the intensity of the second light 122 may be changed. Also, when a part of the first light 112 is refracted and the remainder is reflected, the intensity of the second light 122 may be changed, but it is not limited thereto.

As shown in FIG. 3, a first plane 14 among planes including a normal line of the substrate 200 includes the first light 112, the second light 122 and a region 202 in which the first light 112 is irradiated on the substrate 200. The sensing unit 120 is arranged on the first plane 14 on the substrate supporting table 20 such that an incident angle 22 between the first light 112 and the substrate 200 is equal to a reflection angle 24 between the second light 122 and the substrate 200. That is, the sensing unit 120 is arranged to meet the law of reflection. However, the sensing unit 120 is not limited thereto as far as it can detect an optical signal from the second light 122.

Referring again to FIGS. 1 and 2, the second detection unit 30 measures a potential difference between the substrate 200 and the second detection unit 30, and generates and detects an electrical signal corresponding to the measured potential difference. As an example in which the second detection unit 30 detects an electrical signal, the second detection unit 30 generates and detects an electrical signal using a contact potential difference (CPD), but it is not limited thereto. The second detection unit 30 may measure the contact potential difference using a vibrating contact potential difference (vCPD or vibrating CPD), or a non-vibrating contact potential difference (nvCPD or non-vibrating CPD).

Further, the second detection unit 30 may be parallel to the normal line of the substrate 200, but it is not limited thereto.

Hereinafter, an electrical signal detection method of the second detection unit 30 will be described with reference to FIGS. 4A and 4B.

Referring to FIGS. 4A and 4B, when the second detection unit 30 and the substrate facing the second detection unit 30 having different materials are electrically connected to each other (not shown), electric current flows. That is, when two materials having different work functions are electrically connected to each other, electrons flow from a material having a small work function ($\phi_1$) to a material having a large work function ($\phi_2$). Accordingly, electric charges are accumulated on the materials having different work functions, and a contact potential is formed between the materials having different work functions. The contact potential formed in this case is proportional to a difference between the work functions of two materials.

Supposing that the amount of electric charges accumulated on two materials is Q, the capacitance of a capacitor between two materials is C, and a work function difference or a contact potential between two materials is V ($=\phi_2-\phi_1$), an equation of Q=C*V is established. If the equation is differentiated with respect to time, as C and/or V varies over time, electric current is generated. Accordingly, if one of two materials and/or a distance between two materials varies, electric current is generated in the detection unit. That is, if the measured material changes, the work function $\phi_2$ of the measured material changes. Accordingly, the contact potential V changes, and the electric current changing over time is generated. Further, if a distance between two materials changes, the capacitance C changes. Accordingly, the electric current changing over time is generated. The detection unit detects an electrical signal by the generated electric current.

If the work function $\phi_1$ of the second detection unit 30 is smaller than the work function $\phi_2$ of the substrate 200, electrons flow from the second detection unit 30 to the substrate 200. Accordingly, a surface 3000 of the second detection unit 30 has positive electric charges, and a surface 2000 of the substrate facing the second detection unit 30 has negative electric charges. That is, a contact potential is formed. While the second detection unit 30 measures the contact potential V, if there is another material in the substrate 200, the work function $\phi_2$ is changed. The change of the work function $\phi_2$ causes a variation in the contact potential V, thereby generating the electric current changing over time. Further, a physical defect on the substrate 200 changes a distance between the second detection unit 30 and the substrate 200. The change of the distance causes a variation in the capacitance of the capacitor, thereby generating the electric current changing over time. The second detection unit 30 detects an electrical signal by the generated electrical current, thereby inspecting a defect.

Meanwhile, referring to FIG. 5A, $R_O$ is a width at which the sensing unit 120 can detect an optical signal from the substrate 200, and $R_E$ is a width at which the second detection unit 30 can detect an electrical signal from the substrate 200. The area of a region in which a signal from the substrate can be detected is proportional to a square of $R_O$ (or $R_E$). Generally, the area of a region 206 in which the sensing unit 120 can detect an optical signal is smaller than the area of a region 204 in which the second detection unit 30 can detect an electrical signal. That is, a relationship of $R_E > R_O$ is generally established.

Accordingly, when the sensing unit 120 and the second detection unit 30 perform detection one time, a region of the substrate 200 inspected by the sensing unit 120 and a region of the substrate 200 inspected by the second detection unit 30 do not have the same area. Accordingly, it is required to determine a ratio of the number of inspection times of the sensing unit 120 to the number of inspection times of the second detection unit 30 in consideration of a relationship between $R_E$ and $R_O$. For example, let us suppose that the width $R_E$ is 1 mm, and the width $R_O$ is 200 μm. While the second detection unit 30 inspects a region having a width of 1 mm one time, the sensing unit 120 should perform inspection five times while slightly changing the position on the substrate 200. However, the relationship between $R_E$ and $R_O$ is not limited thereto, and it may be $R_E < R_O$ or $R_E \approx R_O$.

Referring to FIGS. 5A and 5B, the width $R_O$ at which the sensing unit 120 can detect an optical signal is substantially the same as the width $R_E$ at which the second detection unit 30 can detect an electrical signal. That is, the area of a region 206a in which an optical signal from the substrate 200 can be detected is substantially the same as the area of a region 204 in which an electrical signal from the substrate 200 can be detected. Accordingly, the sensing unit 120 and the second detection unit 30 can inspect regions having the same area on the substrate 200 at once. In one embodiment in which the width $R_O$ is substantially the same as the width $R_E$, a distance to the region 206a in which an optical signal from the light source 110 can be detected is set to be different from a focal distance of the light source 110. In the embodiment in which the width $R_O$ is substantially the same as the width $R_E$, light from a light source is defocused. In another embodiment in which the width $R_O$ is substantially the same as the width $R_E$, a plurality of sensing units and/or a plurality of second detection units are used. In still another embodiment in which the width $R_O$ is substantially the same as the width $R_E$, the width RO of the first light emitted from a light source may be adjusted by using an optical system, i.e., a lens, a mirror or the like, but it is not limited thereto.

Hereinafter, a relative motion between the first and the second detection units 10 and 20 and the substrate supporting table 20 will be described with reference to FIG. 6A.

Referring to FIG. 6A, the moving member (not shown) rotates the substrate supporting table 20, and the first detection unit 10 and the second detection unit 30 move in a diameter direction 2010 of the substrate 200.

Specifically, while the substrate supporting table 20 is rotating, the first detection unit 10 detects an optical signal and the second detection unit 30 detects an electrical signal in a circumferential direction 2020 of the substrate 200. Then, the first detection unit 10 and the second detection unit 30 move in the diameter direction 2010. Further, while the substrate supporting table 20 is rotating, the first detection unit 10 detects an optical signal and the second detection unit 30 detects an electrical signal again in the circumferential direction 2020 of the substrate 200.

The diameter direction 2010 of the substrate is oriented from the outside to the inside of the substrate, and the circumferential direction 2020 is represented in a clockwise direction. However, it is not limited thereto, and the first detection unit 10 and the second detection unit 30 may move in different directions.

Referring to FIG. 6B, the moving member (not shown) relatively moves the substrate supporting table 20 in Cartesian coordinates with respect to the first detection unit 10 and the second detection unit 30. That is, the substrate supporting table 20 is moved in a first direction 2030 and/or a second direction 2040 perpendicular to the first direction 2030. In one embodiment, the first detection unit 10 and the second detection unit 30 are fixed and the substrate supporting table 20 moves in Cartesian coordinates such that the first detection unit 10 and the second detection unit 30 respectively detect an optical signal and an electrical signal. In another embodiment, the substrate supporting table 20 is fixed, and the first detection unit 10 and the second detection unit 30 move in Cartesian coordinates to detect an optical signal and an electrical signal. Specifically, the first detection unit 10 and the second detection unit 30 may move in the same direction, or in different directions.

Although the substrate supporting table 20, the first detection unit 10 and the second detection unit 30 rotate or move in Cartesian coordinates in FIGS. 6A and 6B, but it is not limited thereto.

Referring to FIG. 7, the signal processing unit 50 includes a signal determining unit 510, a first storage unit 520, a second storage unit 530 and a third storage unit 540 to detect a chemical defect. The amplifiers 40 are separately provided in front of the signal processing unit 50, but may be included in the signal processing unit 50.

Specifically, the first storage unit 520 and the second storage unit 530 receive an optical signal and an electrical signal respectively from the amplifiers 40. The signal determining unit 510 receives the optical signal and the electrical signal respectively from the first storage unit 520 and the second storage unit 530. The signal determining unit 510 may process an input signal and may transmit the signal to the display unit 60 through the third storage unit 540 or transmit the signal directly to the display unit 60.

The first storage unit 520 processes and stores the input optical signal as a physical defect. The second storage unit 530 processes and stores the input electrical signal as an electrical defect. The first storage unit 520 and the second storage unit 530 respectively transmit the processed optical signal and the processed electrical signal to the signal determining unit 510. The first storage unit 520 and the second storage unit 530 are arranged in front of the signal determining unit 510, but it is not limited thereto.

Further, the signal determining unit 510 detects a chemical defect signal using the signals inputted from the first storage unit 520 and the second storage unit 530. That is, the chemical defect signal is detected using the optical signal from the first detection unit and the electrical signal from the second detection unit. The signal determining unit 510 transmits the detected chemical defect signal to the third storage unit 540. However, if it is not a chemical defect, it is directly transmitted to the display unit 60.

The third storage unit 540 processes and stores the chemical defect signal as a chemical defect. The third storage unit 540 transmits the processed chemical defect signal to the display unit 60.

The signal processing unit 50 may not include the first storage unit 520, the second storage unit 530 and the third storage unit 540. Specifically, the signal determining unit 510 detects a chemical defect using the optical signal and the electrical signal without storing the optical signal and the electrical signal. Then, the optical signal may be transmitted as a physical defect to the display unit 60, the electrical signal may be transmitted as an electrical defect to the display unit 60, and the chemical defect signal may be transmitted as a chemical defect to the display unit 60.

Hereinafter, a function of the signal determining unit 510, i.e., an operation in which the signal determining unit 510 processes the input signal, will be described in brief.

In the defect inspection apparatus in accordance with the embodiment of the present invention, the signal determining unit 510 may classify the types of defects on the substrate using the optical signal detected by the first detection unit and the electrical signal detected by the second detection unit. In another embodiment, when the optical signal and the electrical signal detected in the same region on the substrate have a predetermined time interval, the signal determining unit 510 may shift one of the two signals by a predetermined time interval to classify the types of defects. In still another embodiment, the signal determining unit 510 may remove periodic variations in the optical signal and the electrical signal generated by the pattern in the patterned substrate. The embodiments may be implemented independently or simultaneously. A detailed description thereof will be given later with reference to FIGS. 13A to 13F and 16.

FIG. 8A illustrates an example in which the defects detected by the second detection unit 30 are displayed in the display unit 60. FIG. 8B illustrates an example in which the defects detected by the first detection unit 10 are displayed in the display unit 60. FIG. 8C is an enlarged view of a defect 800 of FIG. 8A.

Comparing FIGS. 8A to 8C, a first portion 750 and a second portion 800 in which the second detection unit detects variations in the electrical signal represent electrical defects. A third portion 750a in which a variation in the optical signal is detected represents a physical defect. However, in the region corresponding to the second portion 800, a variation in the optical signal is not detected. Accordingly, the second portion 800 is a portion corresponding to a chemical defect, and the signal processing unit 50 determines the portion as a chemical defect. Thus, the display unit 60 displays the second portion 800 as a chemical defect. The display unit 60 may sequentially display an electrical defect, a physical defect and a chemical defect, but there is no limitation on the order to display the defects.

A case in which the signal processing unit detects a chemical defect signal using the detected optical signal and electrical signal will be described with reference to FIGS. 9 and 10.

Figures 9, 10:
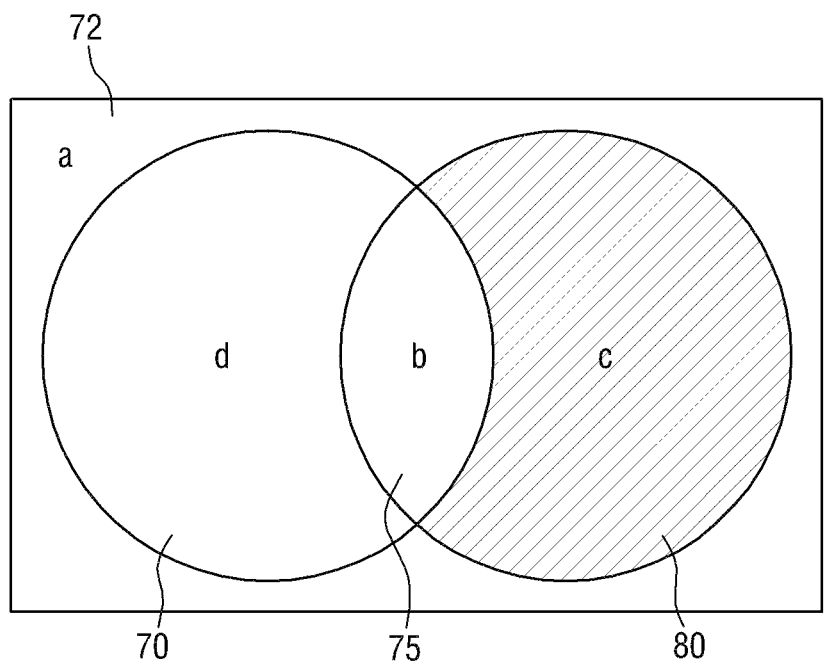
FIG. 9 is a Venn diagram showing a region corresponding to a chemical defect signal in an optical signal and an electrical signal detected on the substrate.
FIG. 10 is a table showing whether a chemical defect is determined from the detected optical signal and electrical signal.

FIG. 9 is a Venn diagram showing a region corresponding to a chemical defect signal in the optical signal and the electrical signal detected on the substrate. FIG. 10 is a table showing whether a chemical defect is determined from the detected optical signal and electrical signal.

Referring to FIG. 9, a first signal 70 corresponds to (d) of FIG. 10, wherein only the first detection unit detects a variation in the optical signal. A second signal 72 corresponds to (a) of FIG. 10, wherein both the first detection unit and the second detection unit do not detect variations in signals. A third signal 75 corresponds to (b) of FIG. 10, wherein the first detection unit and the second detection unit detect variations in the optical signal and the electrical signal respectively. A fourth signal 80 corresponds to (c) of FIG. 10, wherein only the second detection unit detects a variation in the electrical signal.

Hereinafter, explanation of FIG. 10 in a case where the substrate is substantially flat will be given. However, in case of a patterned substrate, if the optical signal and the electrical signal detected by the pattern are removed by the signal processing unit, a signal of the patterned substrate is substantially the same as that of the flat substrate. Accordingly, FIG. 10 may be also applied to the patterned substrate.

Referring to FIG. 10, (a) represents a case where both variations in the optical signal and the electrical signal are not detected. For example, in the case of (a), since there is no physical defect and/or chemical defect on the substrate, there is no variation in the contact potential, there is no scattering of light on the substrate, and a chemical defect is not detected. Further, (b) represents a case where both variations in the optical signal and the electrical signal are detected. For example, in the case of (b), since there is a physical defect on the substrate regardless of a chemical defect, there is a variation in the contact potential, there is scattering of light on the substrate, and a chemical defect is not detected. Further, (c) represents a case where a variation in the optical signal is not detected and a variation in the electrical signal is detected. For example, in the case of (c), since there is only a chemical defect on the substrate, there is a variation in the contact potential, there is no scattering of light on the substrate, and a chemical defect is detected. Further, (d) represents a case where a variation in the optical signal is detected and a variation in the electrical signal is not detected. For example, in the case of (c), since there is a physical defect on the substrate, there is scattering of light on the substrate, but there is no variation in the contact potential, and a chemical defect is not detected. In another case of (c), since there are both a physical defect and a chemical defect, changes in current over time offset each other, only scattering of light occurs on the substrate, and a chemical defect is not detected.

A defect inspection method in accordance with the embodiment of the present invention will be described with reference to FIGS. 11 to 13.

Figure 11:
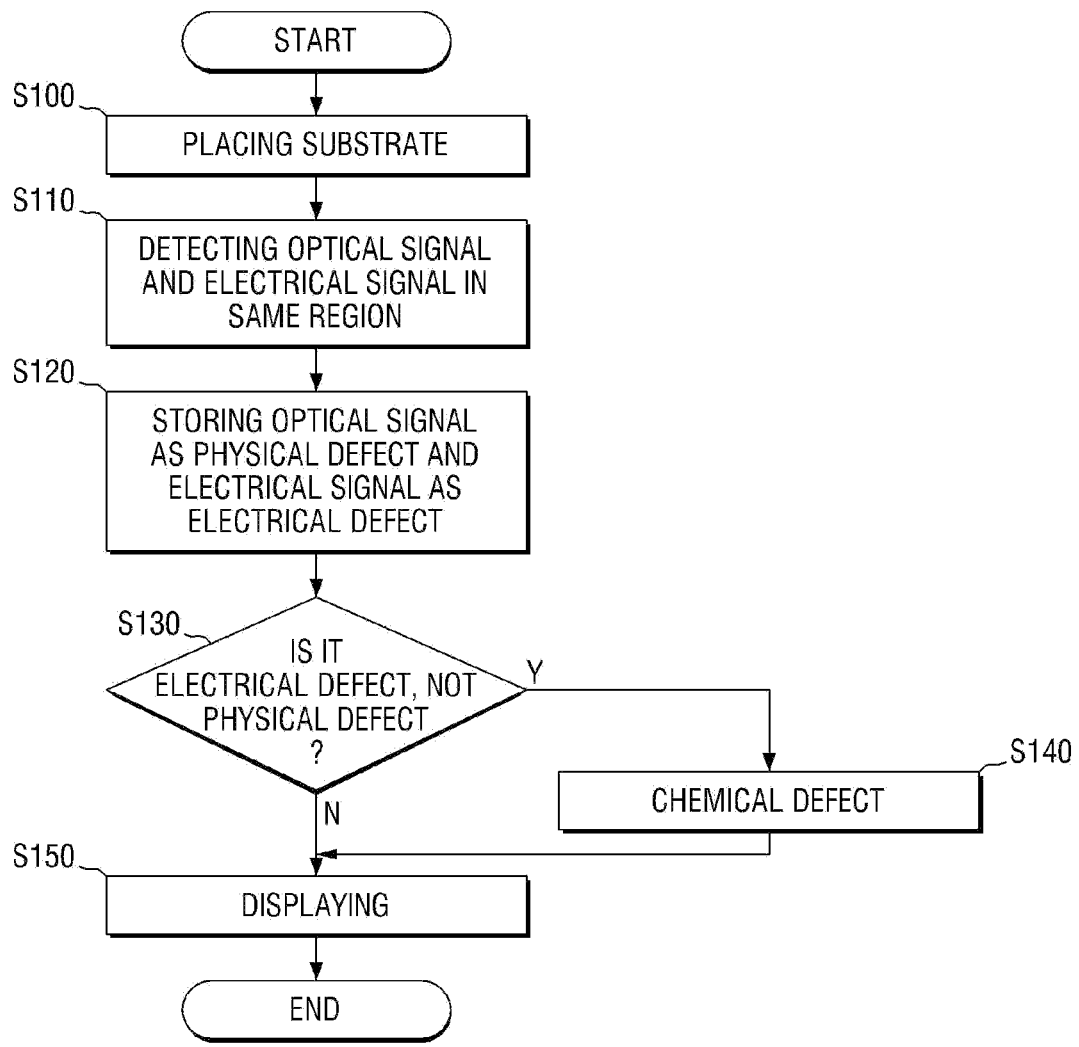
FIGS. 11 to 13F are diagrams for explaining a defect inspection method in accordance with the embodiment of the present invention.
Figure 12A:
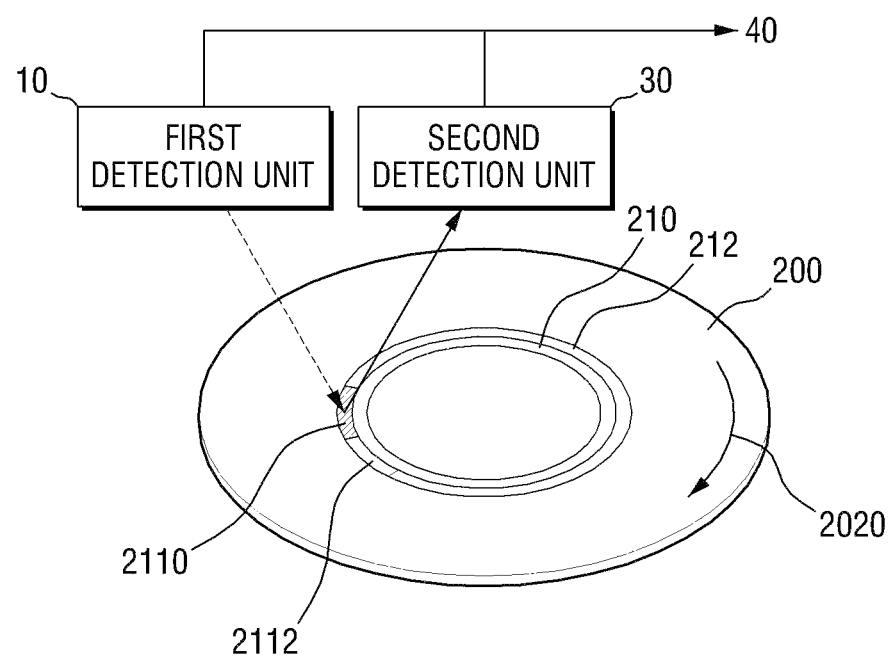
Figure 12B:
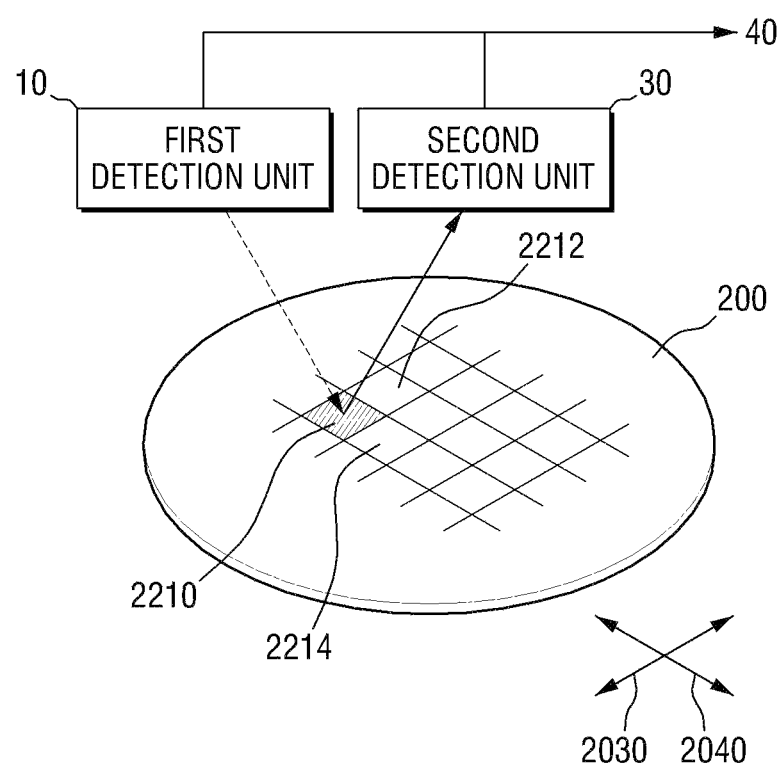
Figure 13A:
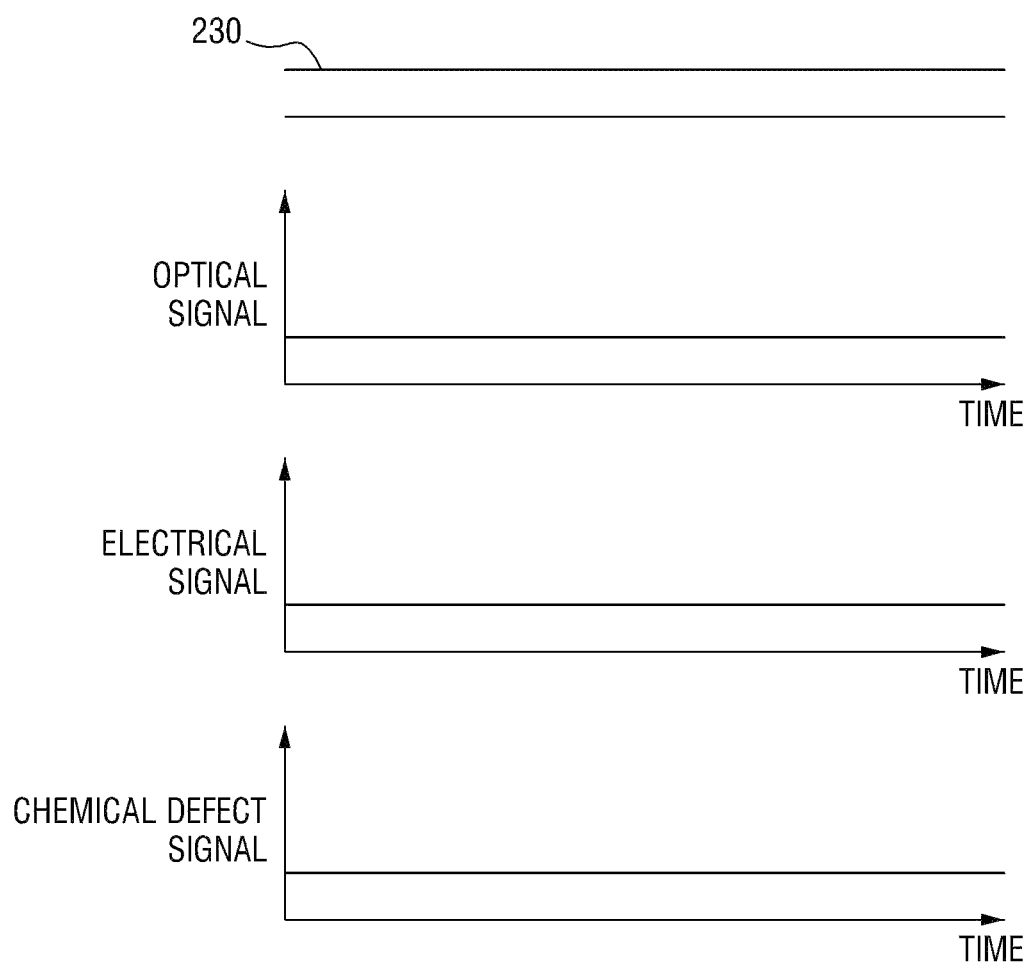
Figure 13C:
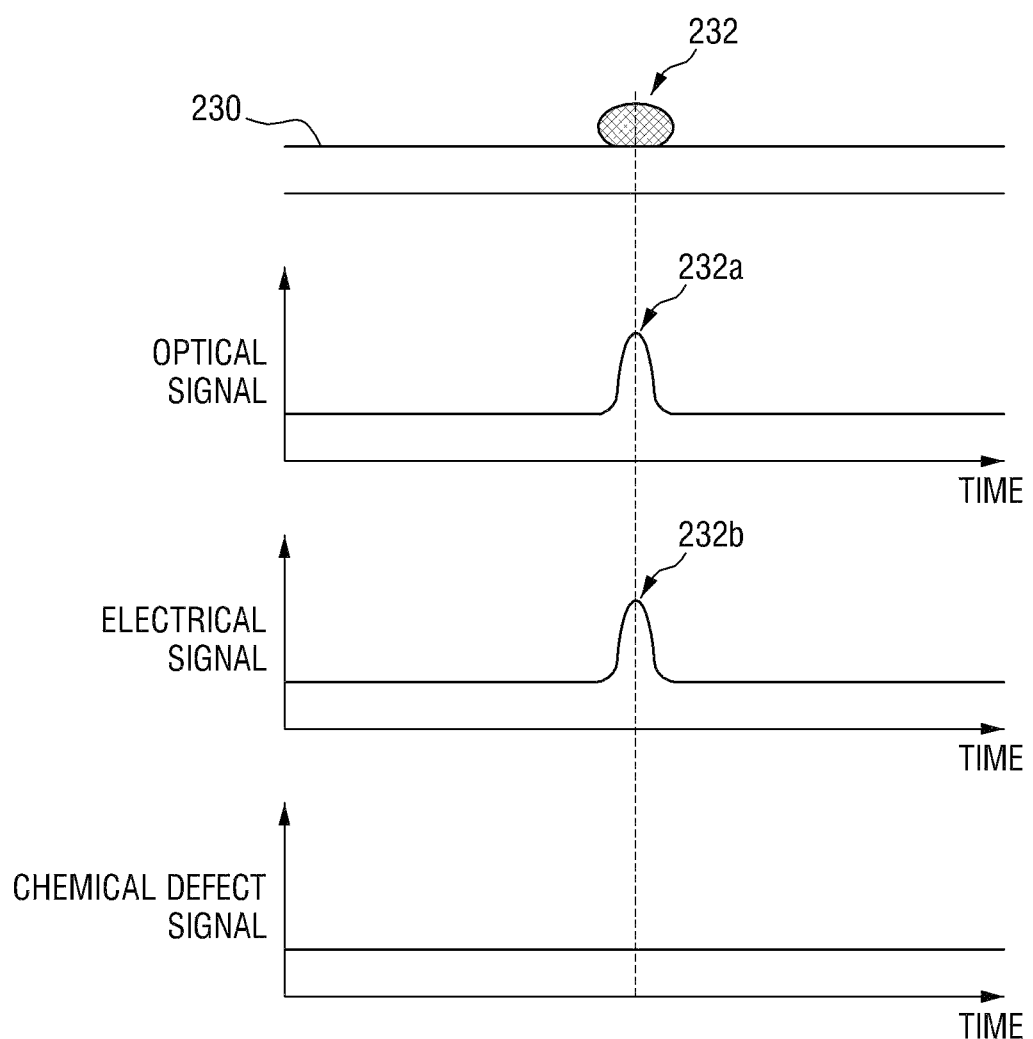
Figure 13D:
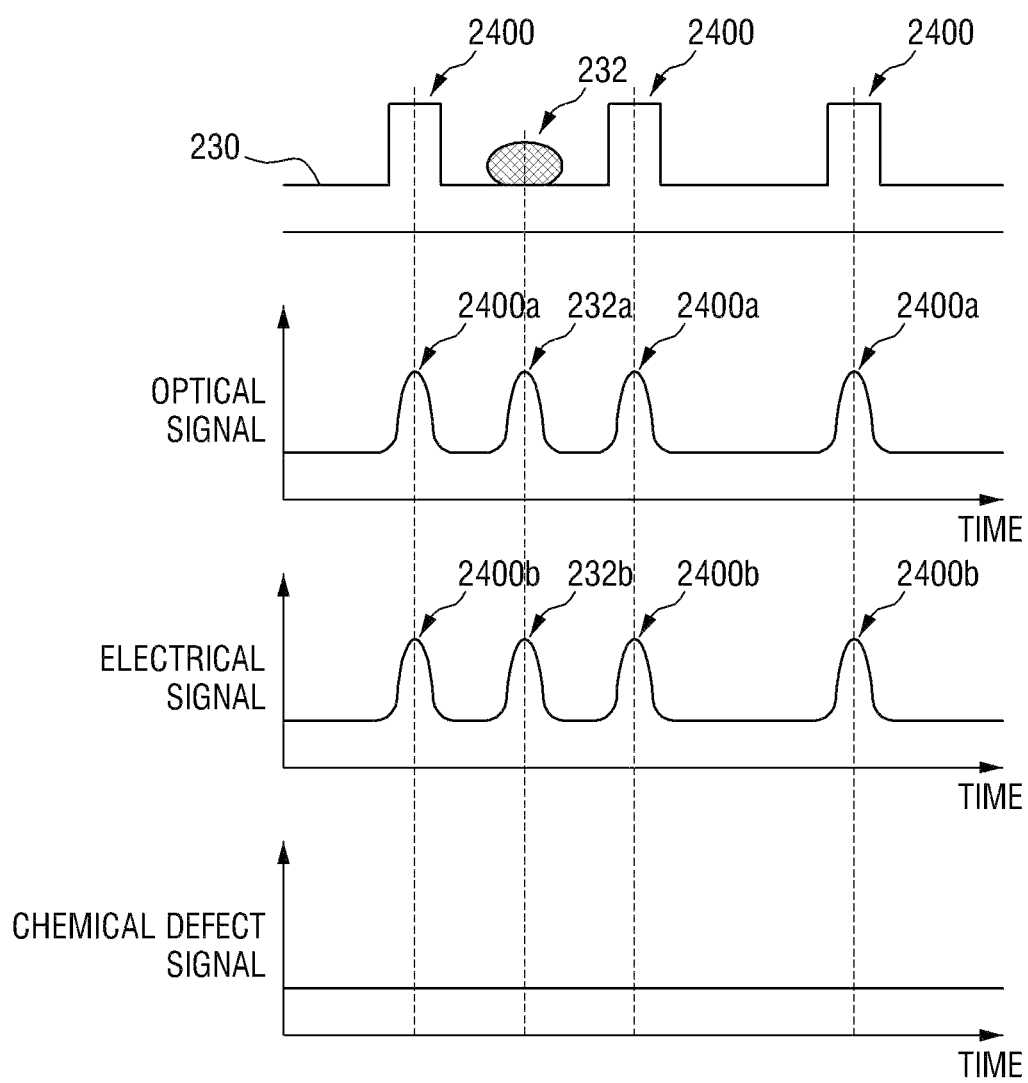
Figure 13F:
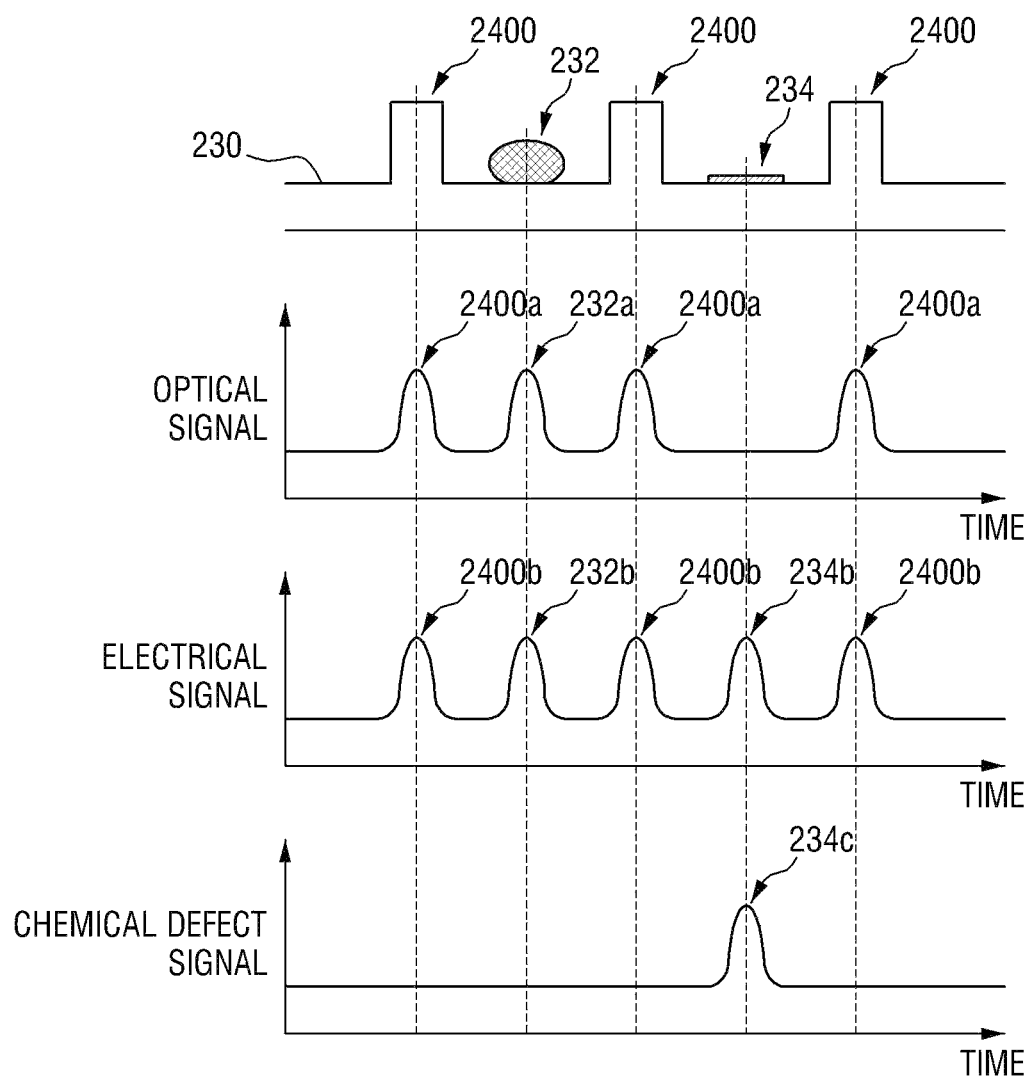

FIG. 11 is a flowchart showing a method of simultaneously detecting an optical signal and an electrical signal in the same region on the substrate to inspect a defect. FIGS. 12A and 12B illustrate a method of inspecting the entire substrate to simultaneously detect an optical signal and an electrical signal in the same region on the substrate. FIGS. 13A and 13F illustrate a method of detecting a chemical defect using the simultaneously detected optical signal and electrical signal.

Referring to FIGS. 2 and 11 to 12B, a substrate to be inspected is placed on the substrate supporting table 20 (step S100). The first detection unit 10 detects an optical signal and the second detection unit 30 detects an electrical signal simultaneously in the same region on the substrate 200 (step S110).

Specifically, in FIG. 12A, while the substrate 200 performs a first rotation, the first detection unit 10 and the second detection unit 30 respectively detect an optical signal and an electrical signal from the substrate 200 in the circumferential direction 2020. That is, the first detection unit 10 detects an optical signal and the second detection unit 30 detects an electrical signal in a first region 2110 of a first circumferential region 212. When the substrate 200 rotates in the circumferential direction 2020, the first detection unit 10 detects an optical signal and the second detection unit 30 detects an electrical signal again in a second region 2112. During the first rotation, the first detection unit 10 and the second detection unit 30 detect an optical signal and an electrical signal in the entire first circumferential region 212. Then, the first detection unit 10 and the second detection unit 30 move in a diameter direction of the substrate. While the substrate 200 performs a second rotation, the first detection unit 10 detects an optical signal and the second detection unit 30 detects an electrical signal again in a second circumferential region 210. By repeating the first rotation and second rotation, the first detection unit 10 detects an optical signal and the second detection unit 30 detects an electrical signal in the entire substrate 200.

The above process may be continuously performed. Further, after measuring the first circumferential region 212, the first detection unit 10 and the second detection unit 30 may move in any direction instead of the diameter direction of the substrate.

In FIG. 12B, the first detection unit 10 detects an optical signal and the second detection unit 30 detects an electrical signal in a region 2210 of the substrate. Then, the substrate 200 moves in Cartesian coordinates with respect to the first detection unit 10 and the second detection unit 30, and the first detection unit 10 detects an optical signal and the second detection unit 30 detects an electrical signal again. That is, when the substrate moves in the first direction 2030 to inspect an adjacent region 2212, moves in the second direction 2040 to inspect an adjacent region 2214, or moves in the first direction 2030 and the second direction 2040 to inspect an adjacent region (not shown), the first detection unit 10 detects an optical signal and the second detection unit 30 detects an electrical signal again.

The above process may be continuously performed, and instead of moving the substrate, the first detection unit 10 and the second detection unit 30 may move, or all of the substrate 200, the first detection unit 10 and the second detection unit 30 may move in Cartesian coordinates. Further, for convenience of explanation, a signal detection region has a rectangular shape in FIG. 12B, but it is not limited thereto.

Referring to FIGS. 7, 11 and 13A to 13F, the optical signal and the electrical signal simultaneously detected in the same region are processed and stored as a physical defect and an electrical defect, respectively (step S120). The signal determining unit 510 determines whether there is a chemical defect using the optical signal and the electrical signal simultaneously detected in the same region on the substrate. That is, the signal determining unit 510 determines a signal, which corresponds to an electrical defect, but does not correspond to a physical defect, as a chemical defect signal (step S130). The detected chemical defect signal is processed and stored as a chemical defect (step S140).

Hereinafter, an embodiment in which the signal determining unit 510 determines whether there is a chemical defect using the optical signal and the electrical signal simultaneously measured in the same region of the substrate will be described.

Further, a pattern signal detected in a patterned substrate 240 is represented as a periodic optical signal 2400a and a periodic electrical signal 2400b. Accordingly, the signal determining unit 510 processes these periodic signals 2400a and 2400b as a pattern signal due to a pattern 2400 on the substrate, and removes the periodic pattern signal. Storing the optical signal, from which the periodic pattern signal is removed, as a physical defect and the electrical signal, from which the periodic pattern signal is removed, as an electrical defect may be included in the step S130 of determining whether there is a chemical defect.

Specifically, in FIG. 13A, there are no physical and chemical defects on a substantially flat substrate 230. Accordingly, there is no variation in the detected optical signal and electrical signal, and the signal determining unit 510 does not detect a chemical defect signal. In FIG. 13C, there is only a physical defect 232 on the substantially flat substrate 230. Accordingly, there are detected an optical signal 232a and an electrical signal 232b due to a physical defect 232. However, the signal determining unit 510 does not detect a chemical defect signal. In FIG. 13E, there are both a physical defect 232 and a chemical defect 234 on the substantially flat substrate 230. Accordingly, there are detected an optical signal 232a and an electrical signal 232b due to the physical defect 232, and an electrical signal 234b due to the chemical defect 234. Further, the signal determining unit 510 detects a chemical defect signal 234c.

In FIG. 13B, although there are no physical and chemical defects on the patterned substrate 240, an optical signal 2400a and an electrical signal 2400b due to a pattern 2400 on the substrate are detected. However, since the signal determining unit 510 processes and removes the optical signal 2400a and the electrical signal 2400b due to a pattern as a pattern signal, the signal determining unit 510 does not detect a chemical defect signal. In FIG. 13D, there is only a physical defect on the patterned substrate 240. There are detected an optical signal 232a and an electrical signal 232b due to the physical defect 232, and an optical signal 2400a and an electrical signal 2400b due to the pattern 2400 on the substrate. However, since the signal determining unit 510 processes and removes the optical signal 2400a and the electrical signal 2400b due to the pattern 2400 as a pattern signal, as shown in FIG. 13C, the signal determining unit 510 does not detect a chemical defect signal. In FIG. 13F, there are both the physical defect 232 and the chemical defect 234 on the patterned substrate 240. There are detected an optical signal 232a and an electrical signal 232b due to the physical defect 232, an electrical signal 234b due to the chemical defect 234, and an optical signal 2400a and an electrical signal 2400b due to the pattern 2400 on the substrate. Since the signal determining unit 510 processes and removes the optical signal 2400a and the electrical signal 2400b due to the pattern as a pattern signal, as shown in FIG. 13E, the signal determining unit 510 detects a chemical defect signal 234c.

After classifying the types of defects, a physical defect, an electrical defect and a chemical defect are displayed on the display unit 60 (S150). In this case, the physical defect and the electrical defect are displayed on a physical defect display unit and an electrical defect display unit, and the chemical defect is displayed on a chemical defect display unit.

The step S120 of storing a physical defect and an electrical defect in the above-described inspection method may be omitted or performed before the step S150 of classifying the types of defects and displaying the defects, and the step S140 of storing a chemical defect may be omitted.

A defect inspection method in accordance with another embodiment of the present invention will be described with reference to FIGS. 14 to 16.

FIG. 14 is a flowchart showing a method of detecting a chemical defect using an optical signal and an electrical signal detected on the substrate. FIGS. 15A to 15D illustrate a method of inspecting the entire substrate to detect an optical signal and an electrical signal on the substrate. FIG. 16 illustrates a method of detecting a chemical defect using an optical signal and an electrical signal detected at a certain time interval.

Referring to FIGS. 2 and 14 to 15D, a substrate to be inspected is placed on the substrate supporting table 20 (step S200). The first detection unit 10 detects an optical signal in a first region on the substrate 200 and the second detection unit 30 detects an electrical signal in a second region on the substrate 200 (step S210).

Figure 15A:
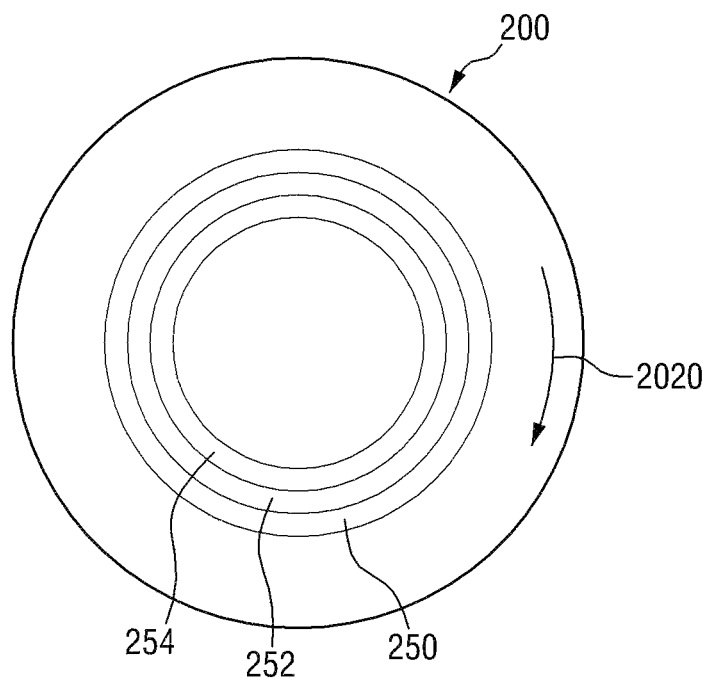
Figure 15B:
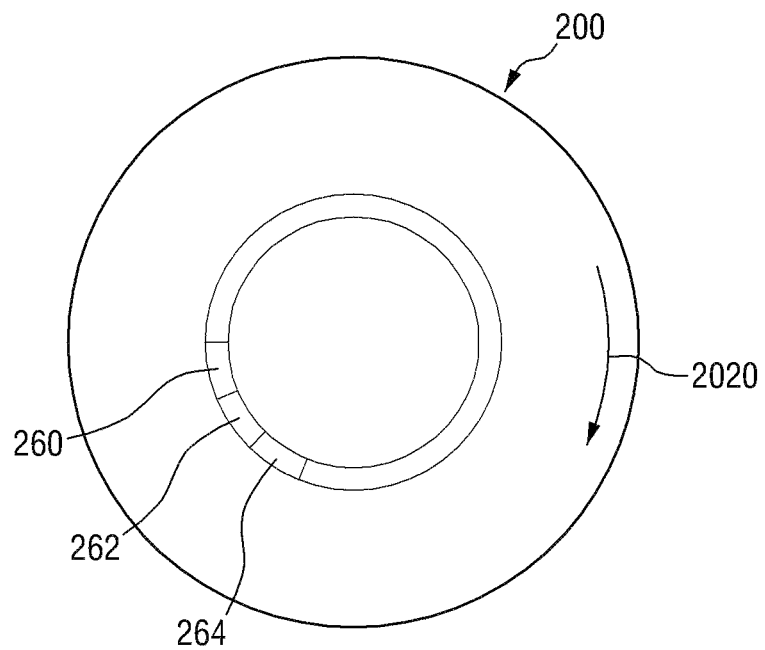
Figure 15C:
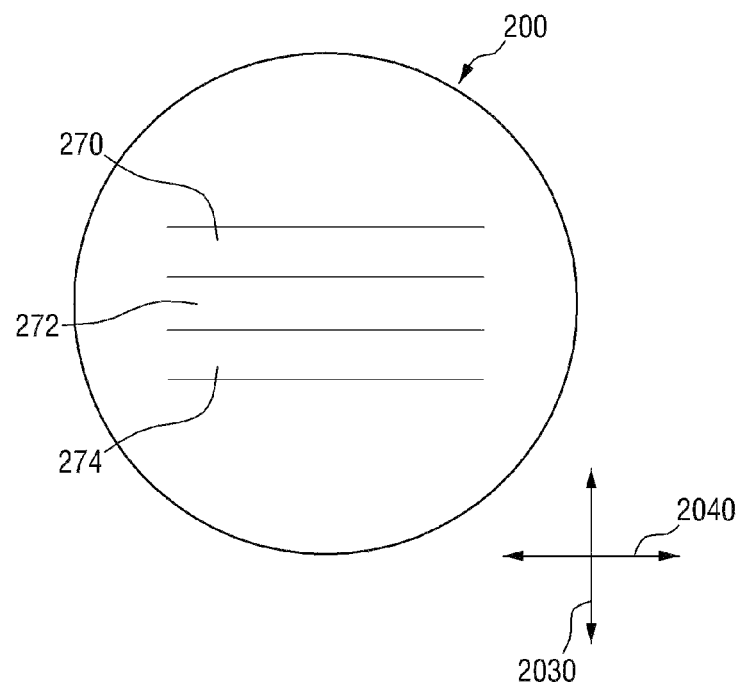
Figure 15D:
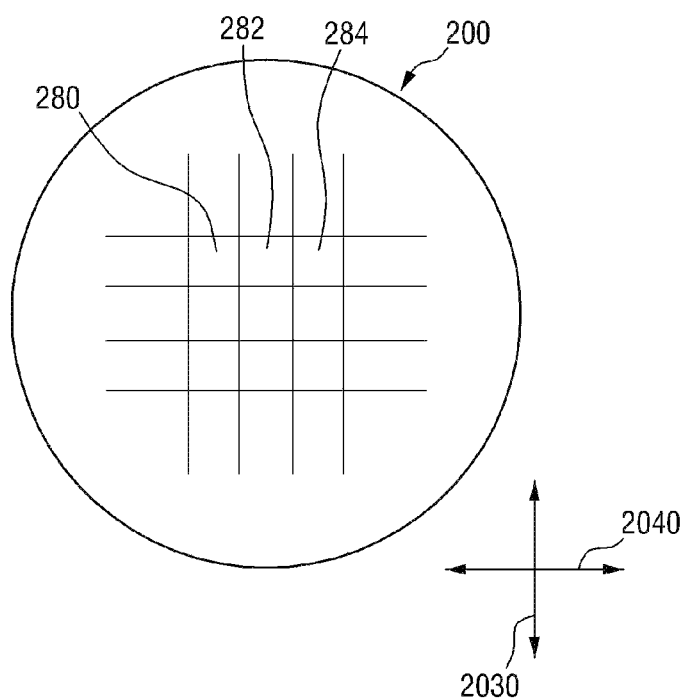

Specifically, in FIG. 15A, while the substrate 200 performs a first rotation, the first detection unit 10 detects an optical signal in a first circumferential region 250, and the second detection unit 30 detects an electrical signal in a second circumferential region 252. Then, after the first detection unit 10 and the second detection unit 30 respectively move, the first detection unit 10 detects an optical signal in the second circumferential region 252, and the second detection unit 30 detects an electrical signal in a third circumferential region. In FIG. 15B, while the substrate rotates, the first detection unit 10 detects an optical signal in a fourth region 260, and the second detection unit 30 detects an electrical signal in a fifth region 262. As the substrate rotates, the first detection unit 10 detects an optical signal in the fifth region 262, and the second detection unit 30 detects an electrical signal in a sixth region 264. In FIGS. 15C and 15D, the first detection unit 10 detects an optical signal in a seventh region 270 and 280, and the second detection unit 30 detects an electrical signal in an eighth region 272 and 282. After moving the first detection unit 10 and the second detection unit 30 to change a signal detection region, the first detection unit 10 detects an optical signal in the eighth region 272 and 282, and the second detection unit 30 detects an electrical signal in a ninth region 274 and 284. The above process may be continuously performed, and the first detection unit detects an optical signal, and the second detection unit detects an electrical signal over the entire substrate. If an optical signal and an electrical signal are simultaneously detected in the same region of the substrate, a description thereof will be omitted because it is the same as that of FIGS. 12A and 12B. Further, for convenience of explanation, a signal detection region has a rectangular shape in FIGS. 15B and 15D, but it is not limited thereto.

Referring to FIGS. 7, 11 and 14 to 16, the optical signal and the electrical signal detected on the substrate are processed and stored as a physical defect and an electrical defect, respectively (step S220). The signal determining unit 510 determines whether there is a chemical defect using the detected optical signal and electrical signal. That is, the signal determining unit 510 determines a signal, which corresponds to an electrical defect, but does not correspond to a physical defect, as a chemical defect signal (step S230). The detected chemical defect signal is processed and stored as a chemical defect (step S240).

Hereinafter, an embodiment in which the signal determining unit 510 determines whether there is a chemical defect using an optical signal and an electrical signal having a certain time interval will be described.

The signal determining unit 510 processes a periodic optical signal and a periodic electrical signal of a patterned substrate as a pattern signal due to a pattern on the substrate, and removes the periodic pattern signal. Storing the optical signal, from which the periodic pattern signal is removed, as a physical defect and the electrical signal, from which the periodic pattern signal is removed, as an electrical defect may be included in the step S230 of determining whether there is a chemical defect.

Further, when the optical signal and the electrical signal are detected at a time interval of Δt in the same region of the substrate, the signal determining unit 510 shifts a signal detected later of the optical signal and the electrical signal, e.g., the electrical signal, by Δt. Then, the signal determining unit 510 determines whether there is a chemical defect using the optical signal and the electrical signal shifted by Δt. On the contrary, after shifting a signal detected earlier of the detected signals by Δt, it may be determined whether there is a chemical defect.

The embodiment in which a chemical defect is determined using an optical signal and an electrical signal simultaneously detected in the same region of the substrate has been described above with reference to FIGS. 13A to 13F, and thus, a repeated description thereof will be omitted. Further, the optical signal from which the pattern signal due to the patterned substrate is removed is substantially the same as an optical signal measured on a flat substrate. Further, the electrical signal from which the pattern signal due to the patterned substrate is removed is substantially the same as an electrical signal measured on a flat substrate, and thus, a description thereof will be omitted.

Figure 16:
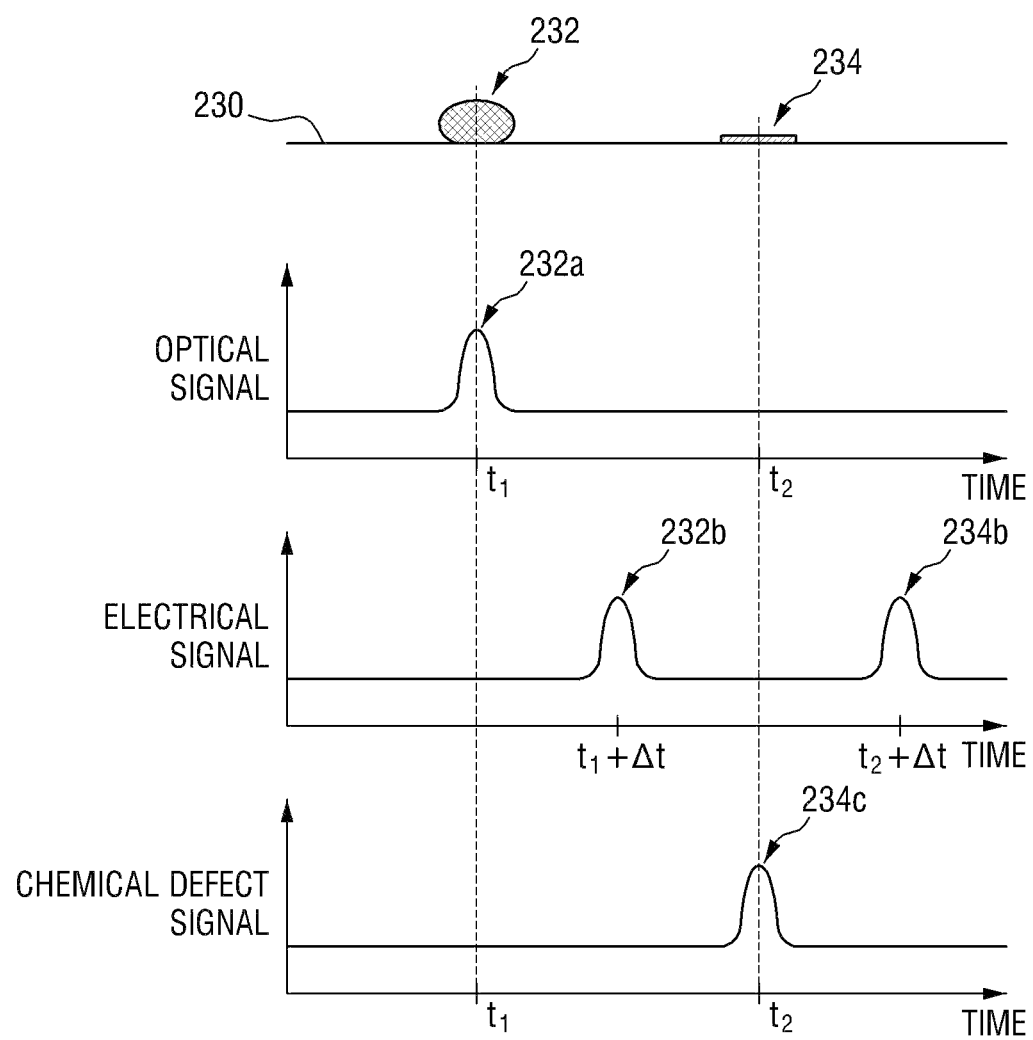

Specifically, referring to FIG. 16, there are both the physical defect 232 and the chemical defect 234 on the substantially flat substrate. The optical signal 232a and the electrical signal 232b are detected at a time t1 and a time t1+Δt, respectively, due to the physical defect 232, and the electrical signal 234b is detected at a time t2+Δt due to the chemical defect 234. The signal determining unit 510 shifts the electrical signal 232b detected at a time t1+Δt due to the physical defect 232 and the electrical signal 234b detected at a time t2+Δt due to the chemical defect 234 by Δt in a negative temporal direction. Further, when it is determined whether there is a chemical defect using the shifted electrical signal (not shown), the signal determining unit 510 detects the chemical defect signal 234c. This means that there is a chemical defect in the region of the substrate in which the optical signal is measured by the first detection unit 10 at a time t2.

After classifying the types of defects, a physical defect, an electrical defect and a chemical defect are displayed on the display unit 60 (S250). In this case, the physical defect and the electrical defect are displayed on a physical defect display unit and an electrical defect display unit, and the chemical defect is displayed on a chemical defect display unit. The step S220 of storing a physical defect and an electrical defect in the above-described inspection method may be omitted or performed before the step S250 of classifying the types of defects and displaying the defects, and the step S240 of storing a chemical defect may be omitted.

While the present invention has been particularly shown and described with reference to exemplary embodiments thereof, it will be understood by those of ordinary skill in the art that various changes in form and detail may be made therein without departing from the spirit and scope of the present invention as defined by the following claims. The exemplary embodiments should be considered in a descriptive sense only and not for purposes of limitation.

What is claimed is:

1. A defect inspection apparatus comprising:
a table on which a substrate is placed;
a first detection unit which is disposed above the table and which detects an optical signal from the substrate;
a second detection unit which is disposed above the table and which detects an electrical signal from the substrate; and
a signal processing unit which is connected to the first detection unit and the second detection unit and which detects a chemical defect using the optical signal and the electrical signal,
wherein the signal processing unit detects a physical defect based on the optical signal, and detects an electrical defect based on the electrical signal, and detects a chemical defect based on an electrical defect which does not correspond to a physical defect.

2. The defect inspection apparatus of claim 1, wherein the first detection unit comprises a light source which irradiates light onto the substrate, and a sensing unit which senses the light reflected from the substrate.

3. The defect inspection apparatus of claim 2, wherein the light source comprises a laser.

4. The defect inspection apparatus of claim 1, wherein the table is electrically connected to a first voltage, and the second detection unit measures a potential difference between the substrate and the second detection unit to generate the electrical signal corresponding to the potential difference.

5. The defect inspection apparatus of claim 4, wherein the second detection unit comprises a contact potential difference sensor.

6. The defect inspection apparatus of claim 1, wherein the first detection unit detects the optical signal from a substantially same region in which the second detection unit detects the electrical signal.

7. The defect inspection apparatus of claim 1, wherein the optical signal and the electrical signal are detected from the substrate during a relative motion between the first and the second detection units and the table.

8. The defect inspection apparatus of claim 7, wherein the table rotates and the first detection unit and the second detection unit move in a diameter direction of the substrate to detect the optical signal and the electrical signal.

9. The defect inspection apparatus of claim 1, wherein the substrate is a patterned substrate and the signal processing unit removes a pattern signal from the optical signal and the electrical signal.

10. A defect inspection apparatus comprising:
a table on which a substrate is placed;
a first detection unit and a second detection unit which are disposed above the table and which detect an optical signal from an inspection region of the substrate and an electrical signal from the inspection region of the substrate, respectively; and
a signal processing unit which is connected to the first detection unit and the second detection unit and which process the optical signal and the electrical signal,
wherein the signal processing unit detects a physical defect based on the optical signal, and detects an electrical defect based on the electrical signal, and detects a chemical defect based on an electrical defect which does not correspond to a physical defect.

11. The defect inspection apparatus of claim 10, wherein the first detection unit comprises a light source which irradiates light onto the substrate, and a sensing unit which senses the light reflected from the substrate.

12. The defect inspection apparatus of claim 10, wherein the table is electrically connected to a first voltage, and the second detection unit measures a potential difference between the substrate and the second detection unit to generate the electrical signal.

13. The defect inspection apparatus of claim 10, wherein the signal processing unit detects the chemical defect using the optical signal and the electrical signal.

14. The defect inspection apparatus of claim 10, wherein the substrate is a patterned substrate and the signal processing unit removes a pattern signal from the optical signal and the electrical signal.

15. The defect inspection apparatus of claim 10 wherein the first detection unit and the second detection unit detect the optical signal and the electrical signal simultaneously.

16. The defect inspection apparatus of claim 10 wherein the first detection unit detects the optical signal from an inspection region of the substrate at a first time and the second detection unit detects the electrical signal of the region of the substrate at a second time that is different from the first time.

17. An apparatus of detecting a chemical defect in a substrate comprising:
a substrate;
an optical sensor which generates an optical signal based on light reflected from a region of the substrate;
an electrical sensor which generates an electrical signal by measuring the voltage difference between the region of the substrate and a fixed voltage; and
a signal processor which detects a chemical defect based on a comparison of the optical signal and the electrical signal,
wherein the signal processor detects a physical defect based on the optical signal, and detects an electrical defect based on the electrical signal, and detects a chemical defect based on an electrical defect which does not correspond to a physical defect.

18. The apparatus of claim 17, wherein the substrate translates relative to the optical sensor and the electrical sensor.

19. The apparatus of claim 17, wherein the substrate rotates and the optical sensor and the electrical sensor translate relative to the substrate.

* * * * *